United States Patent [19]

Coleman et al.

[11] Patent Number: 5,911,985

[45] Date of Patent: *Jun. 15, 1999

[54] PHARMACEUTICAL FORMULATIONS CONTAINING A β-LACTAMASE INHIBITING PENEM IN COMBINATION WITH β-LACTAM ANTIBIOTIC AND THEIR USE IN THE TREATMENT OF BACTERIAL INFECTIONS

[75] Inventors: Kenneth Coleman, Chester Springs, Pa.; Jane Elizabeth Neale, Crawley, United Kingdom

[73] Assignee: SmithKline Beecham p.l.c., Brentford, United Kingdom

[ * ] Notice: This patent is subject to a terminal disclaimer.

[21] Appl. No.: 08/732,379

[22] PCT Filed: Apr. 22, 1995

[86] PCT No.: PCT/EP95/01546

§ 371 Date: Mar. 14, 1997

§ 102(e) Date: Mar. 14, 1997

[87] PCT Pub. No.: WO95/28935

PCT Pub. Date: Nov. 2, 1995

[30] Foreign Application Priority Data

| Apr. 25, 1994 | [GB] | United Kingdom | 9408161 |
| Apr. 25, 1994 | [GB] | United Kingdom | 9408162 |
| Apr. 25, 1994 | [GB] | United Kingdom | 9408163 |
| Apr. 25, 1994 | [GB] | United Kingdom | 9408164 |

[51] Int. Cl.$^6$ .......................... A61K 35/00; A61K 31/43
[52] U.S. Cl. ............................. 424/114; 514/193
[58] Field of Search ............................. 514/193; 424/114

[56] References Cited

U.S. PATENT DOCUMENTS 4,258,041  3/1981  O'Callaghan et al. .

5,602,250  2/1997  Broom et al. ........................ 514/210

FOREIGN PATENT DOCUMENTS

| 0 018 203 | 10/1980 | European Pat. Off. . |
| 0 041 768 | 12/1981 | European Pat. Off. . |
| 0 210 613 | 10/1984 | European Pat. Off. . |
| 0 210 065 | 7/1986 | European Pat. Off. . |
| 0 210 814 | 4/1987 | European Pat. Off. . |
| WO 87/00525 | 1/1987 | WIPO . |
| WO 94/10178 | 5/1994 | WIPO . |

OTHER PUBLICATIONS

Journal of Antibiotics; Coleman et al. vol. 44 No. 3, Mar. 1991, pp. 338–343.

CA 115:2163, 1991.

CA 108:112059, 1987.

*Primary Examiner*—Jerome D. Goldberg
*Attorney, Agent, or Firm*—Edward R. Gimmi; William T. King

[57] ABSTRACT

A pharmaceutical formulation comprises, in combination with a penem of formula (I), in which: $R^1$ is hydrogen or an organic substituent group; $R^2$ is a fused bicyclic heterocyclic ring system of general formula (a), wherein $R^4$ and $R^5$ are independently hydrogen or one or more substituents replacing hydrogen atoms in the ring system shown; m is 2 or 3; p is zero, 1 or 2; and $R^3$ is hydrogen, a salt-forming cation or an ester-forming group; and the symbol ══ indicates that the double bond may be in either the E or Z configuration; and a pharmaceutically acceptable carrier, a β-lactam antibiotic selected from the group consisting of ceftazidime, cefotaxime, amoxycillin, and piperacillin, and pharmaceutically acceptable derivatives thereof.

24 Claims, No Drawings

PHARMACEUTICAL FORMULATIONS CONTAINING A β-LACTAMASE INHIBITING PENEM IN COMBINATION WITH β-LACTAM ANTIBIOTIC AND THEIR USE IN THE TREATMENT OF BACTERIAL INFECTIONS

This Appln. is a 371 of PCT/EP95/01546 filed Apr. 22, 1995.

This invention relates to novel antibacterial formulations, in particular to formulations including 6-(substituted-methylene) penems and derivatives thereof having β-lactamase inhibitory and antibacterial properties. The invention also relates to methods for the preparation of such formulations and to uses thereof.

The compound ceftazidime, [6R-[6α,7β(Z)]]-1-[[7-[[(2-amino-4-thiazolyl)[(1-carboxy-1-methylethoxy)imino]acetyl]amino]-2-carboxy-8-oxo-5-thia-1-azabicyclo[4.2.0]oct-2-en-3-yl]methyl]pyridinium hydroxide inner salt, is a known and much used cephalosporin antibiotic compound. Ceftazidime is normally administered by injection as its pentahydrate. The term "ceftazidime" as used herein includes all forms of ceftazidime including the free acid, hydrates, salts and ester thereof. Ceftazidime is susceptible to hydrolysis by β-lactamase enzymes, for example those of *B. fragilis, S. aureus* and *enterobacteriaceae* producing extended spectrum β-lactamases or elevated levels of Class 1 enzymes.

The compound cefotaxime, [6R-[6α,7β(Z)]]-3-[(acetyloxy)methyl]-7-[[(2-amino-4-thiazolyl)(syn-methoxyimino)acetyl]amino-8-oxo-5-thia-1-azabicyclo[4.2.0]oct-2-ene-2-carboxylic acid, is a known and much used cephalosporin antibiotic compound. Cefotaxime is normally administered by injection as its sodium salt. The term "cefotaxime" as used herein includes all forms of cefotaxime including the free acid, salts and ester thereof. Cefotaxime is susceptible to hydrolysis by β-lactamase enzymes, for example those of *B. fragilis,* Group 1 enzymes (typically encountered in Enterobacter Citrobacter and Pseudomonas), or showing mutational changes around the active site of the Group 2 enzymes TEM-1 and SHV-1 (typically encountered in *E. coli* and Klebsiella.

The compound amoxycillin, 6-[D(-)-α-amino-p-hydroxyphenylacetamido]penicillanic acid, is a known and much used antibiotic compound. Amoxycillin is normally administered orally in the form of amoxycillin trihydrate, or parenterally as sodium amoxycillin. The term "amoxycillin" as used herein includes all forms of amoxycillin including the free acid, salts and ester thereof. Amoxycillin is hydrolysed by a broad range of β-lactamase enzymes, and is generally ineffective against organisms producing Group I and Group II β-lactamases. Therefore amoxycillin is often administered together with a β-lactamase inhibitor, for example clavulanic acid.

The compound piperacillin, 6-[[[[94-ethyl-2,3-dioxo-1-piperazinyl) carbonyl]amino]phenylacetyl]amino]-3,3-dimethyl-7-oxo4-thia-azabicyclo [3.2.0]heptane-2-carboxylic acid, is a known and much used antibiotic compound. Piperacillin is normally administered parenterally as its sodium salt. The term "piperacillin" as used herein includes all forms of piperacillin including the free acid, salts and ester thereof. Piperacillin is hydrolysed by β-lactamase enzymes.

It is an object of this invention to provide novel combinations of β-lactam antibiotics with a β-lactamase inhibitor, having improved characteristics compared with known combinations.

According to the present invention, a pharmaceutical formulation comprises, in combination with a penem of formula (I):

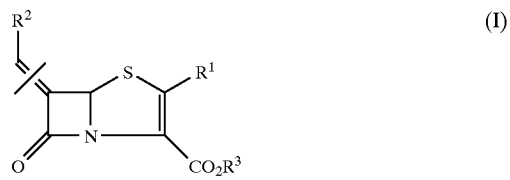

in which:

$R^1$ is hydrogen or an organic substituent group;

$R^2$ is a fused bicyclic heterocyclic ring system of general formula:

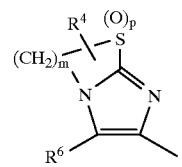

wherein $R^4$ and $R^5$ are independently hydrogen or one or more substituents replacing hydrogen atoms in the ring system shown; m is 2 or 3; p is zero, 1 or 2; and $R^3$ is hydrogen, a salt-forming cation or an ester-forming group; and the symbol $=\!/\!=$ indicates that the double bond may be in either the E or Z configuration; and a pharmaceutically acceptable carrier; a β-lactam antibiotic selected from the group consisting of cefotaxime, amoxycillin, piperacillin and ceftazidime, and their pharmaceutically acceptable derivatives including salts and in vivo hydrolysable esters.

Compounds of formula (I) are disclosed in WO94/10178 the contents of which are incorporated herein by way of reference.

The compound of formula (I), its salts and esters, may exist in a number of isomeric forms, all of which, including racemic and diastereoisomeric forms are encompassed within the scope of the formulations of the present invention.

Moreover, the compounds of formula (I) may exist in two isomeric forms at the methylene group at the 8-position, ie the E- and Z-isomeric forms. The Z-isomer is generally preferred as generally being the more active form.

Consequently preferred forms of the compounds of the present invention have the structure (IA):

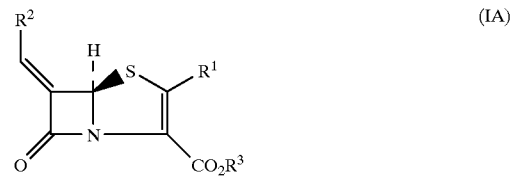

In general formula (I), $R^1$ denotes hydrogen or an organic group, which may suitably be linked through a sulphur or carbon atom. For example, $R^1$ may represent hydrogen or a group of formula $-R^5$ or $-SR^5$, where $R^5$ denotes an unsubstituted or substituted $(C_{1-10})$hydrocarbon or heterocyclyl group.

Preferably, $R^1$ represents hydrogen, $(C_{1-10})$alkyl or $(C_{1-10})$alkylthio, or substituted $(C_{1-10})$alkyl or substituted ($C_{1-10}$)-alkylthio, wherein the substituent may be hydroxy, ($C_{1-6}$)alkoxy, ($C_{1-6}$)alkanoyloxy, halogen, mercapto, ($C_{1-6}$) alkylthio, heterocyclylthio, amino, (mono or di)-($C_{1-6}$) alkylamino, ($C_{1-6}$)alkanoylamino, carboxy, or ($C_{1-6}$) alkoxycarbonyl.

Examples of suitable organic groups $R^1$ include methyl, ethyl, propyl, methylthio, ethylthio, methylsulphinyl, ethylsulphinyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methoxyethylthio, acetoxymethylthio, 2-aminoethylthio, acetamidomethylthio, 2-acetamidoethylthio, carboxymethylthio, 2-carboxyethylthio, aryl (especially phenyl), arylthio (especially phenylthio), pyridyl, pyrimidyl, isoxazolyl, pyrimidylthio, tetrazolylthio, and pyridylthio groups.

In particular, $R^1$ may be hydrogen.

Suitable groups $R^2$ include: 2,3-dihydroimidazo[2,1-b]thiazol-6-yl, 2,3-dihydro-1-(R,S)-oxoimidazo[2,1-b]thiazol-6-yl, 2,3-dihydro-1,1-dioxoimidazo[2,1-b]thiazol-6-yl, 6,7-dihydro-5H-imidazo[2,1-b]-thiazin-2-yl and 6,7-dihydro-8,8-dioxo-5H-imidazo[2,1-b][1,3]thiazin-2-yl.

Examples of suitable substituents $R^4$ and $R^5$ include ($C_{1-6}$)alkanoyl, ($C_{1-6}$)alkanoyloxy, heterocyclyl, amino, ($C_{1-6}$)alkanoylamino, (mono or di)-($C_{1-6}$)alkylamino, hydroxy, ($C_{1-6}$)alkoxy, sulpho, mercapto, ($C_{1-6}$)alkylthio, ($C_{1-6}$)alkylsulphinyl, ($C_{1-6}$)alkyl-sulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted ($C_{1-6}$)alkyl, ($C_{2-6}$)alkenyl, ($C_{2-6}$)alkynyl, aryl, and aryl($C_{1-6}$)alkyl groups.

Examples of suitable optional substituents for the above-mentioned ($C_{1-6}$)alkyl, ($C_{2-6}$)alkenyl, ($C_{2-6}$)alkynyl, aryl and aryl($C_{1-6}$)alkyl substitutents include ($C_{1-6}$)alkanoyl, ($C_{1-6}$)alkanoyloxy, heterocyclyl, amino, ($C_{1-6}$) alkanoylamino, (mono or di)-($C_{1-6}$)alkylamino, hydroxy, ($C_{1-6}$)alkylsulphinyl, ($C_{1-6}$)alkylsulphonyl, heterocyclylthio, arylthio, sulphamoyl, carbamoyl, amidino, guanidino, nitro, halogen, carboxy, carboxy salts, carboxy esters, arylcarbonyl and heterocyclylcarbonyl groups.

Suitably $R^4$ and $R^5$ may both be hydrogen.

Suitable pharmaceutically acceptable salts of the 3-carboxylic acid group of the β-lactam antibiotic or the compound of formula (I) or of other carboxylic acid groups which may be present as optional substituents include those in which $R^3$ is a metal ion e.g. aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g. triethylamine), hydroxy-lower allylanines (e.g. 2-hydroxyethylamine), di(2-hydroxyethyl) amine tri(2-hydroxyethyl)amine), bis-(2-hydroxy ethyl) amine, tris-(2-hydroxyethyl)amine, lower-alkylamines (e.g. dicyclohexylamine), or with procaine, dibenzylamine, N,N-dibenzyl-ethylenediamine, 1-ephenamine, N-methylmorpholine, N-ethylpiperidine, N-benzyl-b-phenethylamine, dehydroabietylamine, ethylenediamine, N,N'-bishydroabietylethylenediamine, bases of the pyridine type (e.g. pyridine, collidine and quinoline), and other amines which have been or can be used to form quaternary ammonium salts with penicillins.

Pharmaceutically acceptable salts may also be acid addition salts of any amino or substituted amino group(s) that may be present as optional substituents on the compound of formula (I), or of any heterocyclic group ring nitrogen atoms. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates. Preferred salts are sodium salts.

When $R^3$ is an ester-forming group it may be a carboxylate protecting group or a pharmaceutically acceptable in-vivo hydrolysable ester.

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^6$ where $R^6$ is aryl or heterocyclyl, or an in vivo hydrolysable ester radical such as defined below.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

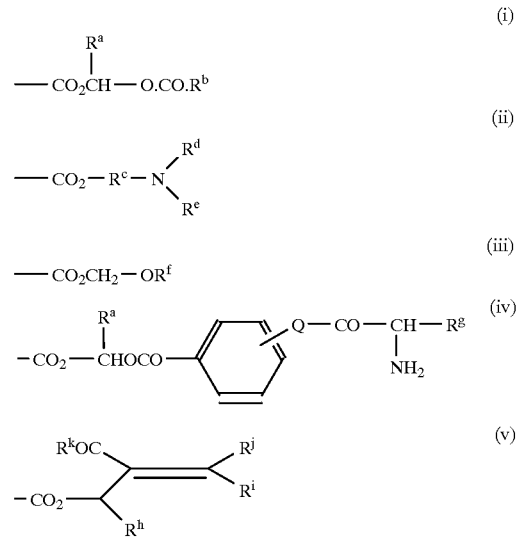

wherein $R^a$ is hydrogen, ($C_{1-6}$) alkyl, ($C_{3-7}$) cycloalkyl, methyl, or phenyl, $R^b$ is ($C_{1-6}$) alkyl, ($C_{1-6}$) alkoxy, phenyl, benzyl, ($C_{3-7}$) cycloalkyl, ($C_{3-7}$) cycloalkyloxy, ($C_{1-6}$) alkyl ($C_{3-7}$) cycloalkyl, 1-amino ($C_{1-6}$) alkyl, or 1-($C_{1-6}$ alkyl) amino ($C_{1-6}$) alkyl; or $R^a$ and $R^b$ together form a 1,2-phenylene group optionally substituted by one or two methoxy groups; $R^c$ represents ($C_{1-6}$) alkylene optionally substituted with a methyl or ethyl group and $R^d$ and $R^e$ independently represent ($C_{1-6}$) alkyl; $R^f$ represents ($C_{1-6}$) alkyl; $R^g$ represents hydrogen or phenyl optionally substituted by up to three groups selected from halogen, ($C_{1-6}$) alkyl, or ($C_{1-6}$) alkoxy; Q is oxygen or NH; $R^h$ is hydrogen or ($C_{1-6}$) alkyl; $R^i$ is hydrogen, ($C_{1-6}$) alkyl optionally substituted by halogen, ($C_{2-6}$) alkenyl, ($C_{1-6}$) alkoxycarbonyl, aryl or heteroaryl; or $R^h$ and $R^i$ together form ($C_{1-6}$) alkylene; $R^j$ represents hydrogen, ($C_{1-6}$) alkyl or ($C_{1-6}$) alkoxycarbonyl; and $R^k$ represents ($C_{1-8}$) alkyl, ($C_{1-8}$) alkoxy, ($C_{1-6}$) alkoxy($C_{1-6}$)alkoxy or aryl.

Examples of suitable in vivo hydrolysable ester groups include, for example, acyloxyalkyl groups such as acetoxymethyl, pivaloyloxymethyl, α-acetoxyethyl, a-pivaloyloxyethyl, 1-(cyclohexylcarbonyloxy)prop-1-yl, and (1-aminoethyl) carbonyloxymethyl; alkoxycarbonyloxyalkyl groups, such as ethoxy carbonyloxymethyl, α-ethoxycarbonyloxyethyl and propoxycarbonyloxyethyl; dialkylaminoalkyl especially di-lower alkylamino alkyl groups such as dimethyl aminomethyl, dimethyl aminoethyl, diethylaminomethyl or diethylaminoethyl; 2-(alkoxy carbonyl)-2-alkenyl groups such as 2-(isobutoxycarbonyl) pent-2-enyl and 2-(ethoxycarbonyl)but-2-enyl; lactone groups such as phthalidyl and dimethoxy phthalidyl; and esters linked to a (second) β-lactam antibiotic or β-lactamase inhibitor.

A further suitable pharmaceutically acceptable in vivo hydrolysable ester group is that of the formula:

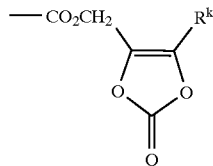

wherein $R^k$ is hydrogen, $C_{1-6}$ alkyl or phenyl.

When used herein the term 'aryl' includes phenyl and naphthyl, each optionally substituted with up to five, preferably up to three, groups selected from halogen, mercapto, ($C_{1-6}$) alkyl, phenyl, ($C_{1-6}$) alkoxy, hydroxy($C_{1-6}$)alkyl, mercapto($C_{1-6}$)alkyl, halo($C_{1-6}$) alkyl, hydroxy, amino, nitro, carboxy, ($C_{1-6}$) alkylcarbonyloxy, alkoxycarbonyl, formyl, or ($C_{1-6}$) alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, ($C_{1-6}$)alkyl, ($C_{1-6}$) alkoxy, halo($C_{1-6}$)alkyl, hydroxy, carboxy, carboxy salts, carboxy esters such as ($C_{1-6}$)alkoxycarbonyl, ($C_{1-6}$) alkoxycarbonyl($C_{1-6}$)alkyl, aryl, and oxo groups. Each heterocyclic ring suitably has from 4 to 7, preferably 5 or 6, ring atoms. The term 'heteroaryl' refers to heteroaromatic heterocyclic ring or ring system, suitably having 5 or 6 ring atoms in each ring. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein the terms 'alkyl', 'alkenyl', 'alkynyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

It will be appreciated that also included within the scope of the invention are formulations which utilise salts and carboxy-protected derivatives, including in vivo hydrolysable esters, of any carboxy groups that may be present as optional substituents in compounds of formula (I).

Certain compounds of formula (I) may include an amino group which may be protected. Suitable amino protecting groups are those well known in the art which may be removed under conventional conditions if required without disruption of the remainder of the molecule.

Examples of amino protecting groups include ($C_{1-6}$) alkanoyl; benzoyl; benzyl optionally substituted in the phenyl ring by one or two substituents selected from ($C_{1-4}$) alkyl, ($C_{1-4}$) alkoxy, trifluoromethyl, halogen, or nitro; ($C_{1-4}$) alkoxycarbonyl; benzyloxycarbonyl or trityl substituted as for benzyl above; allyloxycarbonyl, trichloroethoxycarbonyl or chloroacetyl.

Some compounds of formula (I) and (IA) may be crystallised or recrystallised from solvents such as organic solvents. In such cases solvates may be formed. This invention includes within its scope stoichiometric solvates including hydrates as well as compounds containing variable amounts of solvents such as water that may be produced by processes such as lyophilisation. Compounds of formula (I) and (IA) may be prepared in crystalline form by for example dissolution of the compound in water, preferably in the minimum quantity thereof, followed by admixing of this aqueous solution with a water miscible organic solvent such as a lower aliphatic ketone such as a di-($C_{1-6}$) allyl ketone, or a ($C_{1-6}$) alcohol, such as acetone or ethanol.

The compounds of formula (I) and (IA) are β-lactamase inhibitors and/or antibiotics and are intended for use in pharmaceutical compositions. Therefore it will readily be understood that they are preferably each provided in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or (IA) or ester or salt thereof.

Compounds of formula (I), and in particular of formula (IA) are believed to be active β-lactamase inhibitors, and to have the further advantage of improved pharmacokinetics.

Accordingly, specific compounds of formula (I) include the following pharmaceutically acceptable salts:

Sodium (5R)-6-[(Z)-(2,3-dihydroimidazo[2,1-b]thiazol-6-yl) methylene]penem-3-carboxylate.

Sodium (5R)-6-[(Z)-(2,3-dihydro-1(R,S)-oxoimidazo[2,1-b]thiazol-6-yl)methylene]penem-3-carboxylate.

Sodium (5R)-6-[(Z)-(2,3-dihydro-1,1-dioxoimidazo[2,1-b] thiazol-6-yl)methylene]penem-3-carboxylate.

Sodium (5R)-6-[(Z)-(6,7-dihydro-5H-imidazo[2,1-b][1,3] thiazin-2-yl)methylene]penem-3-carboxylate.

Sodium (5R)-6-[(Z)-(6,7-dihydro-8,8-dioxo-5H-imidazo[2,1-b][1,3]thiazin-2-yl)methylene]penem-3-carboxylate.

Compounds of formula (I) as defined above may be prepared by subjecting a compound of the formula (II):

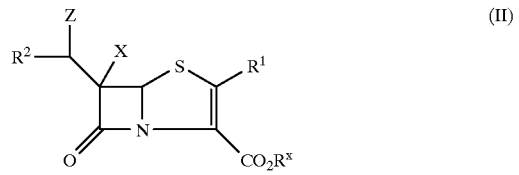

wherein $R^1$ and $R^2$ are as defined in formula (I) above, $R^x$ is a carboxy-protecting group, X is a halogen atom, and Z denotes a halogen atom, a hydroxy group, a substituted hydroxy group, an —S(O)$_q$R$^7$ group or an —Se(O)$_r$R$^7$ group where q denotes 0, 1 or 2, r denotes 0 or 1, and R$^7$ denotes a hydrogen atom, a hydrocarbon group or a heterocyclyl group, to a reductive elimination reaction to eliminate the elements of the group X and Z,
and thereafter if necessary or desired:

(i) converting the group R$^x$ to a different group R$^x$ such as a substituent R$^3$, (ii) converting the group R$^2$ into a different group R$^2$, (iii) converting the group OR$^5$ into a different group OR$^5$.

(iv) converting the compound into a pharmaceutically acceptable salt.

The reductive elimination reaction may be carried out in a manner known per se for such elimination reactions for example as described in EP 0232966A. The elimination may for example be carried out by reaction with a metal, for example zinc, magnesium, aluminium, or iron, in the presence of an acid (for example, acetic acid or a mineral acid), or by reaction with a triorganophosphorus compound, for example triphenylphosphine, suitably at a temperature within the range of from −20° C. to +40° C., preferably from 0° C. to 20° C. The reaction may be carried out in the presence of a polar or non-polar, protic or aprotic, organic solvent, for example dioxane, dimethoxyethane, or tetrahydrofuran.

The product of this reaction is generally a mixture of isomers of the E and Z isomers of formula (I). The desired isomer of the general formula (I) may be isolated and purified in conventional manner for example by known crystallisation or chromatographic techniques. Moreover, the carboxy group —COOR$^x$ may be deprotected, that is to say, converted to a free carboxy, carboxy salt or carboxy ester group —COOR$^3$ in a conventional manner, for example as described in EP0232966A.

When it is desired to obtain a free acid or salt of the preferred penem isomer of the formula (I) from such an isomeric mixture, this may be effected by chromatographic separation of the product followed by deprotection of the desired isomer to give the corresponding free acid or salt. In some cases, however, it has been found particularly convenient first to deprotect the isomeric mixture to give an isomeric mixture of the free acid or salt of formula (I), followed by fractional recrystallisation to give the desired acid or salt isomer.

Compounds of formula (II) in which Z is a hydroxy group may be prepared by the reaction of known (see EP0232966) compounds of formula (III):

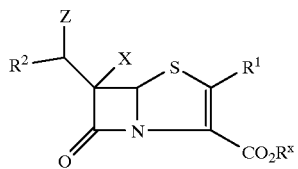
(III)

where X, R$^1$ and R$^x$ are as defined in formula (II), with an aldehyde of formula (IV):

R$^2$—CHO (IV)

where R$^2$ is as defined in formula (II), thereby forming the corresponding halohydrin of formula (II).

The reaction between the compound (III) and the aldehyde (IV) may suitably be carried out in the presence of a base, preferably a non-nucleophilic base, and preferably a strong base. Suitable bases include, for example, lithium amide bases, for example lithium bistrimethyl silylamide, lithium dicyclohexlamide, lithium diisopropylamide, lithium 2,2,6,6-tetramethylpiperidide, lithium diphenylamide, and butyllithium.

Suitable solvents for the reaction are aprotic organic solvents (which may be polar or non-polar), for example tetrahydrofuran, toluene, dimethoxyethane, dimethylformamide, and mixtures of two or more such solvents.

The reaction may suitably be carried out at a temperature within the range of from −100° C. to ambient temperature, preferably from −85° C. to 0° C., especially from −85° C. to 40° C.

The aldehyde of the general formula (IV) and the base may be added to the halo-penem (III) in either order. If it is desired to isolate the halohydrin-penem of the general formula (II) in which Z denotes a hydroxy group, the reaction mixture may conveniently be quenched by adding a protic reagent, for example an acid, such as acetic acid or citric acid, or water.

Aldehydes of formula (IV) may be prepared from known (e.g. Reuben G Jones, CA: (45) 7153e, U.S. Pat. No. 2,541,924) compounds of formula (V):

(V)

where R is allyl, e.g. (C$_{1-6}$) alkyl, and R$^5$ is as defined above, by reaction with known compounds of formula (VI):

X—(CH$_2$)$_m$—Y (VI)

where m is as defined above, and X and Y are halogen, preferably chlorine or bromine. Preferably one of X or Y is chlorine and the other is bromine. A compound of formula (VII) is formed:

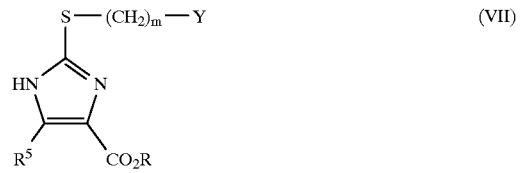
(VII)

The reaction between compounds (V) and (VI) may be carried out in an organic solvent e.g. DMF, in the presence of a base, such as triethylamine.

The compound (VII) may be cyclised, for example by treatment with an alkali metal hydride such as sodium hydride in a solvent such as THF, to form a compound (VIII):

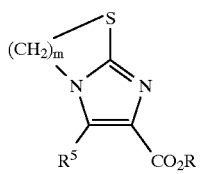

(VIII)

Compounds of formula (VIII) may then be converted to compounds of formula (IV) by various procedures.

For example the $CO_2R$ group of the compound (VIII) may be reduced, using for example di-isobutylaluminium hydride to form the corresponding aldehyde (IV) having p as zero. The corresponding aldehyde (IV) having p as 1 or 2 may then be prepared by oxidation of the S atom using a peroxy acid such as chloroperbenzoic acid.

Alternatively for example the compound (VIII) may be treated with a peroxy acid, e.g. as above, to oxidise the S atom and form the sulphoxide or sulphone analogue of compound (VIII), followed by reduction of the $CO_2R$ group to an aldehyde group e.g. as above to form an aldehyde (IV) having p as 1 or 2.

Alternatively for example the $CO_2R$ group of compound (VIII) may be partly reduced to form the corresponding hydroxymethyl compound (IX):

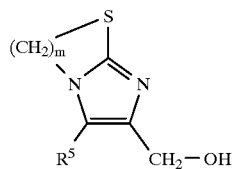

(IX)

for example using lithium aluminium hydride. The hydroxymethyl compound (IX) may then for example be further oxidised, e.g. using Mn(IV), e.g. $MnO_2$, to form the corresponding aldehyde (IV) having p as zero, and which may then be further oxidised using a peroxy acid to form an aldehyde (IV) having p as 1 or 2.

Alternatively the hydroxymethyl compound (IX) may be oxidised using a peroxy acid, e.g. as above to form the corresponding sulphoxide or sulphone (IX), and this sulphoxide or sulphone may then be further oxidised, e.g. using Mn (IV) as above to convert the hydroxymethyl group of (IX) to an aldehyde group, to form an aldehyde (IV) having p as 1 or 2.

Alternatively for example the hydroxymethyl compound (IX) may be acylated to form a compound (X):

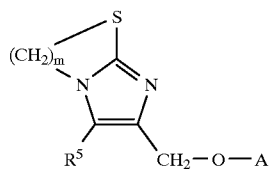

(X)

where A is an acyl group, for example a $(C_{1-6})$ acyl group such as acetyl. Acylation may be by the use of an acylating derivative of A, for example an acyl halide or an acid anhydride. The compound (X) may then be oxidised using a peroxy acid to form the corresponding sulphoxide or sulphone. The hydroxymethyl group may then be regenerated, e.g. by treatment with methanolic ammonia, followed by oxidation of the hydroxymethyl group e.g. using Mn (IV) as above to form the corresponding aldehyde group in an aldehyde (IV).

Compounds of formula (II) in which Z is a substituted hydroxy group or a group of formula $-S(O)_qR^7$ or $-Se(O)_rR^7$ may be prepared from compounds of formula (II) in which Z is hydroxy by known methods, for example as described in EP 0232966A.

When $R^x$ is a carboxylate protecting group, such as 4-methoxybenzyl, these protecting groups may be removed to form the parent acid by methods well known in the art, for example in the case of 4-methoxybenzyl treatment with a Lewis acid such as ethyl aluminium dichloride or aluminium chloride. Pharmaceutically acceptable salts may be prepared from such acids by treatment with a base, after a conventional work-up if necessary. Suitable bases include sodium hydrogen carbonate to form sodium salts.

Crystalline forms of the compounds of formula (I) may for example be prepared by dissolving the compound (I) in the minimum quantity of water, suitably at ambient temperature, then adding a water miscible organic solvent such as a $(C_{1-6})$ alcohol or ketone such as ethanol or acetone, upon which crystalisation occurs and which may be encouraged for example by cooling or trituration.

The compounds of formula (I) have β-lactamase inhibitory and antibacterial properties. Compounds of formula (I) provide β-lactam antibiotics with protection against the β-lactamase enzymes of such microorganisms as *B. fragilis*, *S. aureus*, and strains of Enterobacteriaceae producing extended spectrum β-lactamases, strains producing high levels of Group 1 β-lactamase, *K. pneumoniae*, and *Ent. Cloacae*.

Compounds of formula (I) provide amoxycillin with protection against most of the medically important Group I and Group II β-lactamase producing organisms at in vitro concentrations as low as 0.25 µg/ml. Protection is also observed against problem β-lactamase producing organisms such as high level β-lactamase producing strains of *Ent. Cloacae* P99 and *E. coli* JT4 (Group IIb). Synergy between compounds of formula (I) and amoxycillin is also observed against *B. fragilis*, β-lactamase producing *S. aureus*, and against most Gram negative producing Group II or inducible Group I β-lactamases, and against organisms producing high levels of Group I β-lactamase. Protection against the β-lactamases produced by *Pseudomonas aeruginosa* is also observed.

The pharmaceutical formulations of the invention are useful for the treatment of infections in animals, especially mammals, including humans, in particular in humans and domesticated (including farm)animals. The formulations of this invention may be used, for example, for the treatment of infections for which a β-lactam antibiotic is normally administered, for example of, inter alia, the respiratory tract, urinary tract, and soft tissues, especially in humans. The is formulations of this invention may be used for the treatment of infections caused by strains of, for example, the organisms mentioned above.

Some compounds of formula (I), for example sodium (5R)-6-[(Z)-(2,3-dihydroimidazo[2,1-b]thiazol-6-yl)methylene]penem-3-carboxylate, appear to have an advantageously long serum half life. The compound of formula (I) or (IA) and the β-lactam antibiotic can be administered separately or in the form of a single formulation containing both active ingredients as discussed in more detail below.

The compounds of formula (I) or (IA) may be formulated for administration in any convenient way for use in human or veterinary medicine, by analogy with other antibiotics. The compounds of formula (I), particularly (IA) are particularly suitable for parenteral administration.

The formulation may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound of formula (I), β-lactam and a sterile vehicle, water being preferred. These compounds, depending on the vehicle and concentration used, can be either suspended or dissolved in the vehicle. In preparing solutions these compounds can be dissolved in water for injection and filter sterilised before filling into a suitable vial or ampoule and sealing.

Advantageously, agents such as a local anaesthetic, preservative and buffering agents can be dissolved in the vehicle. To enhance the stability, the formulation can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The formulations may contain from 0.1% by weight, preferably from 10–60% by weight, of the active materials, depending on the method of administration. Where the formulations comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a formulation in accordance with the invention is administered in the above-mentioned dosage range.

A formulation according to the invention may comprise a single β-lactam antibiotic and a compound of formula (I) or (IA) as the sole active ingredients or therapeutic agents, or it may also comprise one or more additional active ingredients or therapeutic agents, for example a second β-lactam antibiotic, or pro-drug thereof.

Ceftazidime may be used in the form of the free acid, e.g. as its pentahydrate.

Cefotaxime may be used in the form of the free acid or its pharmaceutically acceptable salts, for example its sodium salt.

Amoxycillin may be used in the form of amoxycillin trihydrate or its pharmaceutically acceptable salts, for example its sodium salts. Alternatively, amoxycillin may be used in the form of fine particles of its zwitterionic form (generally as amoxycillin trihydrate) for use in an injectable or infusable suspension, for example, in the manner hereinbefore described. Amoxycillin in the form of its sodium salt or the trihydrate is particularly preferred for use in synergistic compositions according to the invention.

Piperacillin may be used in the form of its pharmaceutically acceptable salts, for example its sodium salts, in an injectable or infusable suspension, for example, in the manner hereinbefore described. Piperacillin in the form of its sodium salt is particularly preferred for use in synergistic formulations according to the invention.

A compound of formula (I) or (IA) may be administered to the patient in a synergistically effective amount, together with β-lactam antibiotic.

The compounds of formula (I) or (IA) may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be adminstered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound of formula (I). Each unit dose may, for example, be 62.5, 100, 125, 150, 200 or 250 mg of a compound of formula (I).

The ratio of the amount of the compound of formula (I) to the amount of β-lactam antibiotic(s) may vary within a wide range. The said ratio may, for example, be from 100:1 to 1:100; more particularly, it may, for example, be from 2:1 to 1:30.

The amount of β-lactam antibiotic administered in a formulation according to the invention, i.e in unit doses or the total amount per day will normally be approximately similar to the amount in which it is conventionally used per se.

The amount of cefotaxime in a formulation according to the invention will normally be approximately similar to the amount in which it is conventionally used per se, for example 1–2 g intraveneously or intraveneously every 8 hours, up to a maximum of 12 g daily.

The amount of amoxycillin in a formulation according to the invention will normally be for example from about 50 mg, advantageously from about 62.5 mg, to about 3000 mg per unit dose, more usually about 125, 250, 500, 625, 875 or 1000 mg per unit dose up to the normal maximum with or daily dose of amoxycillin.

The present invention provides a formulation as described above for use as a therapeutic agent.

The present invention further provides a formulation as described above for use in the treatment of bacterial infections.

The present invention includes a method of treating bacterial infections in humans and animals which comprises the administration of a therapeutically effective amount of a formulation as described above.

The present invention also includes the use of formulation as described above, in the manufacture of a medicament for the treatment of bacterial infections, either alone or in combination.

The following Examples illustrate compounds of formula (I), intermediates in their preparation, and synergistic effect of these with β-lactam antibiotics.

PREPARATION 1

2,3-Dihydroimidazo[2,1-b]thiazole-6carboxaldehyde
Method 1 a) Ethyl 2,3-dihydroimidazo[2,1-b]thiazole-6-carboxylate—Ethyl 2-mercaptoimidazole-4(or 5)-carboxylate (1.27 g, 10 mmol) was dissolved in the minimum volume of N,N-dimethylformamide (DMF) and treated with triethylamine (1.11 g, 11 mmol). This solution was added dropwise to a rapidly-stirred solution of 1,2-dibromoethane (9.4 g, 50 mmol) in DMF (5 ml). After 0.5 h, the reaction mixture was poured into a mixture of ethyl acetate (100 ml) and water (50 ml). The organic phase was washed with water (5×50 ml), dried over anhydrous magnesium sulphate and evaporated to dryness under reduced pressure to give an orange oil. Chromatography on silica gel, eluting with mixtures of ethyl acetate in hexane, gave ethyl 2-(2-bromoethylthio)imidazole-4(or 5)-carboxylate as a white solid (1.2 g, 4.3 mmol; 61%).

The above white solid was added portionwise to a stirred suspension of sodium hydride (206 mg of a 50% dispersion in oil, 4.3 mmol) in dry, redistilled tetrahydrofuran (THF) under argon at room temperature. After 0.5 h, the reaction mixture was treated carefully with water (5 ml) and the mixture filtered through Celite. The filtrate was evaporated to dryness under reduced pressure, re-evaporated (2×) with ethanol and purified by chromatography on silica gel, eluting with ethyl acetate, to give the tide compound as a white solid (0.72 g, 81%), mp 107–109° C. (dichloromethane-hexane) (Found: C, 48.25; H, 4.87; N, 14.17; S, 16.34%; M⁺ 198.0465. $C_8H_{10}N_2O_2S$ requires C, 48.48; H, 5.05; N, 14.14; S, 16.16%; 198.0463); $n_{max}$ ($CH_2Cl_2$) 1722, 1703, 1270 and 1260 cm⁻¹; $d_H$ (250 MHz; $CD_3OD$) 1.33 (3H, t, J 7Hz), 3.92 (2H, t, J 7Hz), 4.24–4.38 (4H, m), 7.81 (1H, s).

b) 2,3-Dihydro-6-hydroxymethylimidazo[2,1-b]thiazole—Lithium aluminium hydride (280 mg, 7.3 mmol) was suspended in dry, redistilled THF (20 ml) under argon and treated dropwise with a solution (THF, 20 ml), of ethyl 2,3-dihydroimidazo[2,1-b]thiazole-6-carboxylate (1.32 g, 6.7 mmol). After 2 h, water was added carefully until effervescence ceased when the mixture was filtered through Celite, the filter pad washed with THF and water and the filtrate and washings combined and evaporated to dryness under reduced pressure. The residue was evaporated twice from ethanol to give the title compound as a white solid (1.03 g, 100%); $d_H$ (250 MHz; $CD_3OD$) 3.73–3.95 (2H, m), 4.06–4.30 (2H, m), 4.42 (2H, s), 7.04 (1H, s).

c) 2,3-Dihydroimidazo[2,1-b]thiazole-6-carboxaldehyde—2,3-Dihydro-6-hydroxymethylimidazo[2,1-b]thiazole (1.47 g, 9.4 mmol) was dissolved in acetonitrile (30 ml) by addition of water (minimum volume). Manganese dioxide (4.41 g, 3 wt. equivalents) was added and the mixture stirred at ambient temperatures for 1.5 h. The mixture was filtered through Keiselguhr, the filter pad washed with water and the combined filtrate and washings evaporated to dryness under reduced pressure. The residue was triturated under diethyl ether, the solid collected by filtration and dried in air (1.33 g, 92%); $n_{max}$ ($CH_2Cl_2$) 1685, 1528, 1272, 1260 and 1152 cm⁻¹; $d_H$ (90 MHz; $CD_3OD$) 3.84–4.10 (2H, m), 4.20–4.50 (2H, m), 7.97 (1H, s), 9.52 (1H, s).

Method 2

2,3-Dihydroimidazo[2,1-b]thiazole-6-carboxaldehyde—Ethyl 2,3-dihydroimidazo[2,1-b]thiazole-6-carboxylate (4.2 g; 21.21 mmol) was dissolved in dry dichloromethane (150 ml) and cooled to −70° C. under a stream of dry argon. This solution was treated with a solution of diisobutylaluminium hydride in toluene (1.5M, 26.9 ml, 2 equivalents) over 40 minutes at −70° C. The reaction mixture was stirred at −70° C. for a further 0.5 h. Water (10 ml) was added and the mixture stirred at ambient temperature for 0.5 hr. The mixture was acidified with 5M HCl, filtered through a celite pad and the pad further washed with dichloromethane. The combined organic extracts were dried over anhydrous magnesium sulphate and evaporated to dryness. Chromatography on silica gel, eluting with ethyl acetate, gave the title compound (1.4 g, 43%).

PREPARATION 2

2,3-Dihydroimidazo[2,1-b]thiazole-6-carboxaldehyde-1(R,S)-oxide
Method 1

2,3-Dihydroimidazo[2,1-b]thiazole-6-carboxaldehyde-1(R,S)-oxide—2,3-Dihydroimidazo[2,1-b]thiazole-6-carboxaldehyde (154 mg, 1 mmol) was dissolved in dichloromethane (minimum volume) and the solution cooled to 0–5° C. m-Chloroperbenzoic acid (60% pure, 287.6 mg, 1 mmol) was added and the mixture stirred at 0–5° C. for 0.5 h. Diethyl ether was added, which dissolved the existing precipitate and eventually produced a new precipitate. This new precipitate was collected by filtration, washed with diethyl ether and dried in air (128 mg, 75%) (Found: M⁺ 170.0149. $C_6H_6N_2O_2S$ requires M 170.0150); $n_{max}$ ($CH_2Cl_2$) 1697, 1268 and 1259 cm⁻¹; $d_H$ (250 MHz; $CD_3OD$) 3.69–3.88 (1H, m), 3.94–4.11 (1H, m), 4.50–4.90 (2H, m), 8.20 (1H, s), 9.81 (1H, s).

Method 2 a) 2,3-Dihydro-6-hydroxymethylimidazo[2,1-b]thiazole-1(R,S)-oxide.

2,3-Dihydro-6-hydroxymethylimidazo[2,1-b]thiazole (1.5 g, 10 mmol) in dichloromethane (500 ml) was cooled to 0–5° C. and treated with m-chloroperbenzoic acid (60% pure, 2.88 g, 10 mmol). After 15 minutes, the volatiles were removed under reduced pressure and the residue triturated with diethyl ether. The solvent was decanted and the process repeated twice. The residual solid was dissolved in methanol (minimum volume), filtered and the filtrate evaporated to dryness under reduced pressure to yield an off-white foam (1.64 g, 99%) (Found: M⁺ 172.0308. $C_6H_8N_2O_2S$ requires M 172.0306); $d_H$ [250 MHz; (CD$_3$)$_2$SO] 3.58–3.67 (1H, m), 3.89–4.01 (1H, m), 4.39–4.63 (4H, m), 5.14 (1H, t, J 6Hz), 7.41 (1H, s).

b) 2,3-Dihydroimidazo[2,1-b]thiazole-6-carboxaldehyde-1(R,S)-oxide.

2,3-Dihydro-6-hydroxymethylimidazo[2,1-b]thiazole-1 (R,S)-oxide (376 mg, 2.19 mmol) was suspended in acetonitrile (10 ml) and water was added to obtain a clear solution. Manganese dioxide (1.13 g, 3 wt. equivalents) was added and the mixture stirred vigorously at ambient temperatures for 24 h. More manganese dioxide (1 g) was added and the mixture stirred for a further 24 h. The reaction mixture was filtered through Celite, the filter pad washed with water and the filtrate evaporated to dryness under reduced pressure to give a white solid (340 mg, 91%).

PREPARATION 3

2,3-Dihydroimidazo[2,1-b]thiazole-6-carboxaldehyde-1,1-dioxide a) 6-Acetoxymethyl-2,3-dihydroimidazo[2,1-b]thiazole 2,3-Dihydro-6-hydroxymethylimidazo[2,1-b]thiazole (312 mg, 2 mmol) was suspended in dichloromethane (10 ml) and treated with pyridine (174 mg, 2.2 mmol) and acetic anhydride (224 mg, 2.2 mmol). 4-Dimethylaminopyridine (10 mg) was added and the mixture stirred at ambient temperature for 4 h. The volatiles were removed by evaporation to dryness under reduced pressure and the residue was triturated under hexane, the hexane decanted (2x) and the residue chromatographed on silica gel, eluting with mixtures of ethyl acetate and hexane to give the product (374 mg, 94%) as a white solid; (Found: M$^+$ 198.0465. C$_8$H$_{10}$N$_2$O$_2$S requires M 198.0463); n$_{max}$ (CH$_2$Cl$_2$) 1734 and 1258 cm$^{-1}$; $d_H$ (250 MHz; CDCl$_3$) 2.08 (3H, s), 2.80 (2H, t, J 7Hz), 4.15 (2H, t, J 7Hz), 4.97 (2H, s), 7.11 (1H, s).

b) 6-Acetoxymethyl-2,3-dihydroimidazo[2,1-b]thiazole-1,1-dioxide

6-Acetoxymethyl-2,3-dihydroimidazo[2,1-b]thiazole (358 mg, 1.81 mmol) was dissolved in dichloromethane (10 ml) and treated at room temperature with m-chloroperbenzoic acid (60% pure, 936 mg, 3.78 mmol). After the initial sulphoxidation was complete, the reaction mixture was heated under reflux for 4 h then left to stand at ambient temperature for 72 h. The volatiles were removed under reduced pressure and the residue triturated under diethyl ether and the solvent decanted. This process was repeated (2x) and the residual white solid dissolved in methanol and adsorbed onto silica gel. Chromatography on silica gel, eluting with mixtures of ethyl acetate and hexane, gave the title compound as a white solid (305 mg, 73%) (Found: M$^+$ 230.0361. C$_8$H$_{10}$N$_2$O$_4$S requires M 230.0361); n$_{max}$ (CH$_2$Cl$_2$) 1739, 1336, 1272, 1264 and 1258 cm$^{-1}$; $d_H$ (250 MHz; CDCl$_3$) 2.08 (3H, s), 3.94 (2H, t, J 6Hz), 4.55 (2H, t, J 6Hz), 5.07 (2H, s), 7.16 (1H, s).

c) 2,3-Dihydro-6-hydroxymethylimidazo[2,1-b]thiazole-1,1-dioxide

6-Acetoxymethyl-2,3-dihydroimidazo[2,1-b]thiazole-1,1-dioxide (305 mg, 1.33 mmol) was treated with methanolic ammonia (prepared by saturating methanol (20 ml) with ammonia gas then diluting with more methanol (20 ml)) at room temperature. After 2.5 h, the volatiles were removed under reduced pressure and the residue triturated with diethyl ether and the resulting solid collected by filtration, washed with diethyl ether and dried in air (207 mg, 83%) (Found: M$^+$ 188.0256. C$_6$H$_8$N$_2$O$_3$S requires M 188.0256); n$_{max}$ (nujol) 3354, 1377, 1325 and 1133 cm$^{-1}$; $d_H$ [250 MHz; (CD$_3$)$_2$SO] 4.14 (2H, t, J 6Hz), 4.40 (2H, d, J 6Hz), 4.54 (2H, t, J 6Hz), 5.20 (1H, t, J 6Hz, exchangeable), 7.36 (1H, s).

d) 2,3-Dihydroimidazo[2,1-b]thiazole-6-carboxaldehyde-1,1-dioxide 2,3-Dihydro-6-hydroxymethylimidazo[2,1-b]thiazole-1,1-dioxide (207 mg, 1.1 mmol) was dissolved in acetonitrile (minimum volume) and treated with manganese dioxide (621 mg, 3 wt. equivalents) and the mixture stirred vigorously at ambient temperature. After 1 h, more manganese dioxide (621 mg) was added and the mixture stirred for a further 18 h. The mixture was filtered through Celite, the filter bed washed with acetonitrile, the filtrate and washings combined and evaporated to dryness under reduced pressure. The residue was triturated under dichloromethane and the resulting solid collected by filtration, washed with dichloromethane and dried in air (108 mg, 53%) (Found: M$^+$ 186.0103. C$_6$H$_6$N$_2$O$_3$S requires M 186.0099); n$_{max}$ (Nujol) 1691, 1320 and 1132 cm$^{-1}$; $d_H$ [250 MHz; (CD$_3$)$_2$SO] 4.25 (2H, t, J 7Hz), 4.68 (2H, t, J 7Hz), 8.32 (1H, s), 9.81 (1H, s).

PREPARATION 4

6,7-Dihydro-5H-imidazo[2,1-b][1,3]thiazine-2-carboxaldehyde a) Ethyl 6,7-dihydro-5H-imidazo[2,1-b][1,3]thiazine-2-carboxylate Ethyl 2-mercaptoimidazole-4(or 5)-carboxylate (860 mg, 5 mmol) was dissolved in DMF (minimum volume) containing triethylamine (555 mg, 5.5 mmol). This solution was added dropwise to rapidly-stirred 1,3-dibromopropane (5 ml). After 0.5 h the reaction mixture was partitioned between ethyl acetate and water. The phases were separated and the organic phase washed with water (3x), saturated brine, dried over anhydrous magnesium sulphate and evaporated to dryness under reduced pressure. Chromatography on silica gel, eluting with 25% ethyl acetate-hexane gave the intermediate ethyl 2-(3-bromo-1-propylthio)imidazole-4(or 5)-carboxylate, which was dissolved in dry, redistilled THF (minimum volume) and added dropwise to a stirred suspension of sodium hydride (60% dispersion in oil, 240 mg, 6 mmol) in dry, redistilled THF (20 ml) under argon. After 10 minutes, water was carefully added to the reaction mixture, which was filtered through Celite. The filter bed was washed with THF and the filtrate and washings combined and evaporated to dryness under reduced pressure. Chromatography on silica gel, eluting with 50% ethyl acetate in hexane, gave the title compound as a white solid (635 mg, 60%) mp 99–100° C. (dichloromethane-hexane) (Found: C, 50.86; H, 5.74; N, 13.14; S, 15.07%; M$^+$ 212.0619. C$_9$H$_{12}$N$_2$O$_2$S requires C, 50.94; H, 5.66; N, 13.21; S, 15.09% 212.0619); n$_{max}$ (CH$_2$Cl$_2$) 1720, 1212 and 1198 cm$^{-1}$; $d_H$ (250 MHz; CDCl$_3$) 1.34 (3H, t, J 7Hz), 2.29–2.38 (2H, m), 3.13–3.17 (2H, m), 4.09 (2H, t, J 6Hz), 4.33 (2H, q, J 7Hz), 7.53 (1H, s).

b) 6,7-Dihydro-5H-imidazo[2,1-b][1,3]thiazine-2-carboxaldehyde

Ethyl 6,7-dihydro-5H-imidazo[2,1-b][1,3]thiazine-2-carboxylate (2.12 g, 10 mmol) was dissolved in dry dichloromethane (40 ml) under argon and cooled to 70%. Diisobutylaluminium hydride (1.5M in toluene, 12 ml, 18 mmol) was added below −68° C. and the reaction mixture stirred at −70° C. for 1 h. Water was added carefully and the cooling removed. The reaction mixture was stirred vigorously at ambient temperature for 15 minutes and Celite (2 g) added.

The mixture was filtered through Celite, the filter bed washed with dichloromethane and water, the filtrate and the washings combined and evaporated to dryness under reduced pressure. The residue was evaporated from ethanol (2×) to give the title compound as a white solid (1.31 g, 78%); $n_{max}$ (CH$_2$Cl$_2$) 1685, 1543 and 1453 cm$^{-1}$; $d_H$ (250 MHz; CDCl$_3$) 2.34–2.43 (2H, m), 3.20 (2H, t, J 6Hz), 4.17 (2H, t, J 6Hz), 7.58 (1H, s), 9.75 (1H, s).

PREPARATION 5

6,7-Dihydro-5H-imidazo[2,1-b][1,3]thiazine-2-carboxaldehyde-8,8-dioxide a) Ethyl 6,7-dihydro-5H-imidazo[2,1-b][1,3]thiazine2-carboxylate-8,8-dioxide Ethyl 6,7-dihydro-5H-imidazo[2,1-b][1,3]thiazine-2-carboxylate (212 mg, 1 mmol) in dichloromethane (20 ml) was treated with m-chloroperbenzoic acid (50% pure, 690 mg, 2 mmol). The initial sulphoxidation was rapid and exothermic and, when the sulphoxidation reaction was complete, the mixture was heated under reflux for 2 h. The volatiles were removed under reduced pressure and the residue triturated under diethyl ether. The resulting white solid was collected by filtration, washed with diethyl ether and dried in air (226 mg, 93%) (Found: M$^+$ 244.0521. C$_9$H$_{12}$N$_2$O$_4$S requires M 244.0518); $n_{max}$ (CH$_2$Cl$_2$) 1735, 1717, 1331, 1270, 1257, 1218, 1198, 1167 and 1120 cm$^{-1}$; $d_H$ (250 MHz; CDCl$_3$) 1.36 (3H, t, J 7Hz), 2.71–2.80 (2H, m), 3.54–3.59 (2H, m), 4.28–4.42 (4H, m), 7.65 (1H, s).

b) 6,7-Dihydro-5H-imidazo[2,1-b][1,3]thiazine-2-carboxaldehyde-8,8-dioxide

Ethyl 6,7-dihydro-5H-imidazo[2,1-b][1,3]thiazine-2-carboxylate-8,8-dioxide (200 mg, 0.82 mmol) was dissolved in dry dichloromethane (minimum volume) under argon and cooled to −70° C. Diisobutylaluminium hydride (1.5M in toluene, 1 ml, 1.5 mmol) was added at <−70° C. and the mixture stirred at −70° C. until thin layer chromatography and infra-red spectroscopy showed little or no starting material remaining. Water (5 ml) was added carefully, cooling removed and the mixture stirred at ambient temperature for 1 h. Celite was added to the mixture and the resulting mixture filtered through a Celite pad. The Celite pad was washed with dichloromethane and water and the filtrate and washings combined and evaporated to dryness under reduced pressure. The residue was re-evaporated with ethanol (2×), triturated under diethyl ether and the product collected by filtration, washed with diethyl ether and dried in air (274 mg, 30%) (Found: M$^+$ 200.0256. C$_7$H$_8$N$_2$O$_3$S requires M 200.0253); $n_{max}$ (Nujol) 1678, 1316, 1161 and 1191 cm$^{-1}$; $d_H$ [250 MHz; (CD$_3$)$_2$SO] 2.50–2.57 (2H, m), 3.81–3.85 (2H, m), 4.31 (2H, t, J 6Hz), 8.27 (1H, s), 9.80 (1H, s).

EXAMPLE 1

Sodium (5R)-6-[(Z)-(2,3-dihydroimidazo[2,1-b]thiazol-6-yl) methylene]penem-3-carboxylate a) 4-Methoxybenzyl [5R,6RS,8RS]-6-[acetoxy(2,3-dihydroimidazo[2,1-b]thiazol-6-yl)methyl]-6-bromopenem-3-carboxylate Diphenylamine (604 mg, 3.57 mmol) was dissolved in dry, redistilled THF (35 ml) under argon and cooled to −20° C. n-Butyllithium (1.48M in hexane; 208 mg, 3.25 mmol) was added and the mixture stirred at ambient temperature for 10 minutes. The mixture was cooled to −70° C. and treated dropwise with a solution of 4-methoxybenzyl (5R,6R)-6-bromopenem-3-carboxylate (1.2 g, 3.25 mmol) in dry, redistilled THF (10 ml). The resulting mixture was stirred at −70° C. for 10 minutes then treated with a solution of 2,3-dihydroimidazo[2,1-b]thiazole-6-carboxaldehyde (500 mg, 3.25 mmol) in dry DMF (5 ml). The resulting mixture was stirred at −70° C. for 20 minutes then treated with acetic anhydride (331 mg, 3.25 mmol) and 4-dimethylaminopyridine (100 mg). When all the bromohydrin intermediate had been converted to the title compound, the reaction mixture was concentrated to low volume under reduced pressure and partitioned between dichloromethane and water. The organic phase was separated and washed repeatedly with water (5×), dil. aq. sodium hydrogencarbonate, water, saturated brine, dried (MgSO$_4$) and evaporated to dryness under reduced pressure to give a brown oil. Chromatography on silica gel, eluting with 50% ethyl acetate in hexane, gave the title compound as a brown foam (1.0 g, 55%); $n_{max}$ (CH$_2$Cl$_2$) 1801, 1753 and 1715 cm$^{-1}$.

b) 4-Methoxybenzyl (5R)-6-(2,3-dihydroimidazo[2,1-b]thiazol-6-yl)-methylene]penem-3-carboxylate 4-Methoxybenzyl [5R,6RS,8RS]-6-[acetoxy(2,3-dihydroimidazo[2,1-b]thiazol-6-yl)methyl]-6-bromopenem-3-carboxylate (930 mg, 1.65 mmol) was dissolved in THF (20 ml) and treated with N,N,N',N'-tetramethylethylenediamine (TMEDA, 478 mg, 4.1 mmol) followed by zinc powder (269 mg, 4.1 gm atoms). The mixture was stirred vigorously and treated with glacial acetic acid (247 mg, 4.1 mmol). After 10 minutes, more glacial acetic acid (247 mg, 4.1 mmol) was added and, after a further 10 minutes, the reaction mixture was partitioned between ethyl acetate and water and the resulting mixture filtered through Celite. The phases were separated and the organic phase washed with 1M aq. potassium hydrogensulphate (3×), saturated brine, saturated, aq. sodium hydrogencarbonate (2×), saturated brine, dried (MgSO$_4$) and evaporated to dryness under reduced pressure. The residue was chromatographed on silica gel, eluting with 50% ethyl acetate in hexane, to give the product as a yellow foam (459 mg, 65%); $[a]^D_{25}$+522° (c=0.1% in acetonitrile); $n_{max}$ (CH$_2$Cl$_2$) 1773, 1709, 1252 and 1232 cm$^{-1}$; $d_H$ [250 MHz; (CD$_3$)$_2$CO] 3.79 (3H, s), 3.93 (2H, t, J 7Hz), 4.34 (2H, t, J 7Hz), 5.16 (2H, ABq, J 12.5Hz), 6.55 (1H, d, J 1Hz), 6.91–6.96 (3H, m), 7.40 (2H, d, J 7Hz), 7.45 (1H, s), 7.61 (1H, s).

c) Sodium (5R)-6-[(Z)-(2,3-dihydroimidazo[2,1-b]thiazol-6-yl) methylene]penem-3-carboxylate Anisole (1.52 ml, 14 mmol) was dissolved in dry dichloromethane (2 ml) under argon and the solution cooled to −20° C. Ethyl aluminium dichloride (1.8M in toluene, 147 mg, 1.16 mmol) was added and the mixture stirred at −20° C. for 10 minutes before cooling to −70° C. This mixture was treated, dropwise, with a solution of 4-methoxybenzyl (5R)-6-[(Z)-(2,3-dihydroimidazo[2,1-b]thiazol-6-yl) methylene]penem-3-carboxylate (166 mg, 0.39 mmol) in dry dichloromethane (5 ml). After 15 minutes at −70° C., the mixture was treated with an excess of 0.5M, aqueous trisodium citrate and cooling removed. When the reaction mixture had regained room temperature, it was treated with diethyl ether, acetone and water until two clear phases were obtained with very little material on the interface. The phases were separated and the organic phase extracted with dilute, aqueous sodium hydrogencarbonate. The combined aqueous extracts were acidifed to pH 2 with 5M hydrochloric acid in the presence of ethyl acetate and the phases separated. The aqueous phase was further extracted with ethyl acetate and the combined extracts washed repeatedly with water (5×). The washed organic phase was stirred in the presence of water and the pH of the aqueous phase adjusted to 6.6 by addition of dilute aqueous sodium hydrogencarbonate and the phases separated. The organic phase was further extracted with water and the aqueous extracts combined and freeze-dried. The resulting, orange powder was purified by chromatography on Diaion HP20SS resin, eluting with mixtures of THF in water, to give, after freeze-drying, the title compound as a yellow solid (56.2 mg, 44%); $n_{max}$ (KBr) 1741, 1670, 1597, 1394, 1304 and 1268 cm$^{-1}$; $l_{max}$ (H$_2$O) 325 (e dm$^3$ mol$^{-1}$ cm$^{-1}$ 13,514) and 237 (9768) nm; $d_H$ (250 MHz; D$_2$O) 3.86 (2H, d, J 7Hz), 4.22 (2H, t, J 7Hz), 6.46 (1H, s), 6.86 (1H, s), 7.01 (1H, s), 7.47 (1H, s).

EXAMPLE 2

Sodium (5R)-6-[(Z)-(2,3-dihydro-1(R,S)-oxoimidazo[2,1-b]thiazol-6-yl)methylene]penem-3-carboxylate a) 4-Methoxybenzyl (5R)-6-[(Z)-(2,3-dihydro-1(RS)-oxoimidazo[2,1-b]thiazol-6-yl)methylene]penem-3-carboxylate Diphenylamine (372 mg, 2.2 mmol) was dissolved in dry, redistilled THF (10 ml) under argon and cooled to −20° C. n-Butyllithium (2.5M in hexane, 128 mg, 2 mmol) was added and the mixture stirred at ambient temperatures for 10 minutes. The resulting reaction mixture was cooled to −70° C. and treated dropwise with a solution of 4-methoxybenzyl (5R,6R)-6-bromopenem-3-carboxylate (740 mg, 2 mmol) in dry, redistilled THF (10 ml). After twenty minutes at −70° C., the reaction mixture was treated with a solution of 2,3-dihydroimidazo[2,1-b]thiazole-6-carboxaldehyde-1(RS)-oxide (340 mg, 2 mmol) in dry DMF (5 ml), stirred at −70° C. for 0.5 h then treated with acetic anhydride. Cooling was removed and the mixture stirred at ambient temperatures for 1 h before being partitioned between ethyl acetate and water. The organic phase was washed well with water (5×), saturated brine, dried (MgSO$_4$) and evaporated to dryness under reduced pressure. The residue was purified by chromatography on silica gel, eluting with ethyl acetate, to give the intermediate 4-methoxybenzyl [5R,6RS,8RS]-6-[acetoxy(2,3-dihydro-1(RS)-oxoimidazo[2,1-b]thiazol-6-yl)methyl]-6-bromopenem-3-carboxylate (527 mg, 45%, 0.9 mmol).

The above mixture of bromoacetates (0.9 mmol) was dissolved in THF (10 ml) and treated with TMEDA (263 mg, 2.3 mmol) followed by zinc powder (148 mg, 2.3 g atoms). Glacial acetic acid (136 mg, 2.3 mmol) was added and the mixture stirred vigorously for 10 minutes before more glacial acetic acid (136 mg, 2.3 mmol) was added. After a further 10 minutes the mixture was diluted with ethyl acetate and water and filtered through Celite. The phases in the filtrate were separated, the aqueous phase further extracted with ethyl acetate, the extracts combined, washed with 1M, aqueous potassium hydrogensulphate (3×), saturated brine, saturated, aqueous sodium hydrogencarbonate (2×), saturated brine, dried (MgSO$_4$) and evaporated to dryness under reduced pressure. The residue was chromatographed on silica gel, eluting with ethyl acetate then mixtures of ethanol in ethyl acetate, to give a mixture of (E) and (Z)-isomers, plus pure Z-isomer. The mixture of isomers was rechromatographed on silica gel and the two fractions of pure (Z)-isomer combined (236 mg, 27%); $[a]^P_{25}$+409° (c=0.1% in acetonitrile); $n_{max}$ (KBr) 1772, 1703, 1233 and 1057 cm$^{-1}$; $d_H$ [250 MHz; (CD$_3$)$_2$CO] 3.67–3.76 (1H, m), 3.81 (3H, s), 4.00–4.14 (1H, m), 4.62–4.87 (2H, 2m), 5.18 (2H, s), 6.60 (1H, d, J 1Hz), 6.65 (1H, d, J 1Hz), 6.91–6.97 (2H, m), 7.14 (1H, s), 7.38–7.43 (2H, m), 7.51 and 7.52 (1H, 2s), 7.89 and 7.90 (1H, 2s); m/z (F.A.B., positive ion xenon, NOBA sodium) 482 (MNa$^+$).

b) Sodium (5R)-6-[(Z)-(2,3-dihydro-1(RS)-oxoimidazo[2,1-b]thiazol-6-yl)methylene]penem-3-carboxylate Anisole (499 mg, 4.6 mmol) was dissolved in dry dichloromethane (0.5 ml) under argon and treated with aluminium trichloride (61.5 mg, 0.45 mmol). When a complete solution had been obtained, the mixture was cooled to −40° C. and treated with a solution of 4-methoxybenzyl (5R)-6-[(Z)-(2,3-dihydro-1(RS)-oxoimidazo[2,1-b]thiazol-6-yl)methylene] penem-3-carboxylate (68 mg, 0.15 mmol) in dry dichloromethane (2 ml). After 15 minutes at −40° C., 0.5M trisodium citrate (10 ml) was added and cooling was removed. The mixture was stirred at ambient temperature for 15 minutes and the phases separated. The aqueous phase was washed with dichloromethane then acidified to pH 2 with 5M hydrochloric acid in the presence of ethyl acetate. The phases were separated, the aqueous phase further extracted with ethyl acetate, the extracts combined, washed with water (5×) then stirred vigorously in the presence of water while the pH of the aqueous phase was adjusted to 6.8 with dilute, aqueous sodium hydrogencarbonate. The phases were separated, the organic phase extracted with water, the extracts combined and freeze-dried to give the product (23 mg, 43%); $l_{max}$ (H$_2$O) 370.5 (e dm$^3$ mol$^{-1}$ cm$^{-1}$ 1761) and 301.5 (18,005) nm; $n_{max}$ (KBr) 1751, 1598, 1383, 1268, 1139, 1090 and 1047 cm$^{-1}$; $d_H$ (250 MHz; D$_2$O) 3.83–3.91 and 4.01–4.18 (each 1H, 2m), 4.57–4.66 (1H, m), 6.55 and 6.60 (each 1H, 2d, J 1H), 7.00 (1H, s), 7.09 (1H, s), 7.77 and 7.80 (each 1H, 2s).

EXAMPLE 3

Sodium (5R)-6-[(Z)-(2,3-dihydro-1,1-dioxoimidazo[2,1-b]thiazol-6-yl)methylene]penem-3-carboxylate a) 4-Methoxybenzyl (5R)-6-[(Z)-(2,3-dihydro-1,1-dioxoimidazo[2,1-b]thiazol-6-yl)methylene]penem-3-carboxylate Diphenylamine (372 mg, 2.2 mmol) was dissolved in dry, redistilled THF (10 ml) under argon, cooled to −20° C. and treated with n-butyllithium (2.5M in hexane, 128 mg, 2 mmol). The mixture was stirred at ambient temperature for 10 minutes then cooled to −70° C. A solution of 4-methoxybenzyl (5R,6R)-6-bromopenem-3-carboxylate (740 mg, 2 mmol) in dry, redistilled THF (5 ml) was added dropwise and, after a further 10 minutes at −70° C., a solution of 2,3-dihydroimidazo[2,1-b]thiazole-6-carboxaldehyde-1,1-dioxide (372 mg, 2 mmol) in dry DMF (5 ml) was added to the reaction mixture. This mixture was stirred at −70° C. for 0.5 h then treated with acetic anhydride (204 mg, 2 mmol). Cooling was removed and the mixture stirred at ambient temperture for 1.25 h before being partitioned between ethyl acetate and water. The organic phase was washed with water (4×), saturated brine, dried (MgSO$_4$) and evaporated to dryness under reduced pressure to yield a brown foam. Chromatography on silica gel, eluting with mixtures of ethyl acetate in hexane, gave the bromoacetate intermediate as a mixture of diastereoisomers (504 mg, 0.84 mmol).

The diastereoisomeric mixture of bromoacetates (504 mg, 0.84 mmol) was dissolved in THF (5 ml) and treated with TMEDA (216 mg, 1.9 mmol). Zinc powder (121 mg, 1.9 gm atoms) was added, the mixture stirred vigorously and treated with glacial acetic acid (112 mg, 1.9 mmol). After 10 minutes, more glacial acetic acid (112 mg, 1.9 mmol) was added and after a further 0.5 h, the mixture was partitioned between ethyl acetate and water, filtered through Celite and the phases separated. The organic phase was washed with 1M aqueous potassium hydrogensulphate (3×), saturated brine, saturated aqueous sodium hydrogencarbonate, saturated brine, dried (MgSO$_4$) and evaporated to dryness under reduced pressure. Chromatography of the residue on silica gel, eluting with mixtures of ethyl acetate in hexane, gave the title compound (250 mg, 27%); $[a]^P{}_{25}$+464° (c=0.1% in acetonitrile); n$_{max}$ (CH$_2$Cl$_2$) 1770, 1714, 1274 and 1256 cm$^{-1}$; d$_H$ [250 MHz; (CD$_3$)$_2$CO] 3.81 (3H, s), 4.18 (2H, t, J 7Hz), 4.87 (2H, t, J 7Hz), 5.19 (2H, brs), 6.57 (1H, s), 6.95 (2H, d, J 8Hz), 7.41 (2H, d, J 8Hz), 7.65 (1H, s), 8.39 (1H, s); m/z (F.A.B., +ve ion xenon, NOBA sodium) 482 (MNa$^+$).

a) Sodium (5R)-6-[(Z)-(2,3-dihydro-1,1-dioxoimidazo[2,1-b]thiazol-6-yl)methylene]penem-3-carboxylate Anisole (1.8 g, 16.3 mmol) was dissolved in dry dichloromethane (2 ml) under argon and treated with aluminium trichloride (218 mg, 1.63 mmol). When a complete solution had been obtained, the mixture was cooled to −40° C. and treated with a solution of 4-methoxybenzyl (5R)-6-[(Z)-(2,3-dihydro-1,1-dioxoimidazo[2,1-b]thiazol-6-yl)methylene]penem-3 carboxylate (250 mg, 0.54 mmol) in dry dichloromethane (2 ml). The resulting mixture was stirred at −40° C. for 10 minutes then treated with 0.5M aqueous trisodium citrate (15 ml) and the cooling removed. After a further 15 minutes, the mixture was diluted with diethyl ether, acetone and water until two clear phases were obtained. The phases were separated, the aqueous phase washed with diethyl ether then acidified to pH 2 with 5M hydrochloric acid in the presence of ethyl acetate. The phases were separated, the aqueous phase further extracted with ethyl acetate and the extracts combined. The combined extracts were washed well with water (4×) then stirred vigorously in the presence of water, while the pH of the aqueous phase was adjusted to 6.8 with dilute sodium hydrogencarbonate. The phases were separated, the organic phase further extracted with water, the combined aqueous extracts freeze-dried then purified by chromatography on Diaion HP20SS resin, eluting with mixtures of THF in water, to give the title compound (114 mg, 58%); l$_{max}$ (H$_2$O) 370 (e dm$^3$ mol$^{-1}$ cm$^{-1}$ 2127) and 296.5 (25,942) nm; n$_{max}$ (KBr) 1755, 1599, 1389, 1322, 1269 and 1136 cm$^{-1}$; d$_H$ (KBr) 1755, 1599, 1389, 1322, 1269 and 1136 cm$^{-1}$; d$_H$ (250 MHz; D$_2$O) 4.20 (2H, t, J 7Hz), 4.66 (2H, t, J 7Hz), 6.47 (1H, d, J 1Hz), 6.98 (1H, s), 7.04 (1H, s), 7.64 (1H, s).

EXAMPLE 4

Sodium (5R)-6-[(Z)-(6,7-dihydro-5H-imidazo[2,1-b][1,3]thiazin-2-yl)methylene]penem-3-carboxylate a) 4-Methoxybenzyl (5R,6RS,8RS)-6-[acetoxy(6,7-dihydro-5H-imidazo[2,1-b][1,3]thiazin-2-yl)methyl]-6-bromopenem-3-carboxylate Diphenylamine (589 mg, 3.5 mmol) was dissolved in dry, redistilled THF (20 ml) under argon and the solution cooled to −20° C. n-Butyllithium (2.5M in hexane, 203 mg, 3.2 mmol) was added and the mixture stirred at ambient temperature for 10 minutes before being cooled to −70° C. A solution of 4-methoxybenzyl (5R,6R)-6-bromopenem-3-carboxylate (1.17 g, 3.2 mmol) in dry, distilled THF (10 ml) was added dropwise at −70° C. and the resulting mixture stirred at −70° C. for 10 minutes. A solution of 6,7-dihydro-5H-imidazo[2,1-b][1,3]thiazine-2-carboxaldehyde (532 mg, 3.2 mmol) in dry, redistilled THF (20 ml) was added dropwise at −70° C. and the resulting mixture stirred at −70° C. for 20 minutes. Acetic anhydride (323 mg, 3.2 mmol) then 4-dimethylaminopyridine (20 mg) were added and the cooling removed. After 1 h at ambient temperature, the volatiles were removed under reduced pressure and the residue partitioned between ethyl acetate and water. The organic phase was washed with saturated aqueous sodium hydrogencarbonate, water, saturated brine, dried (MgSO$_4$) and evaporated to dryness under reduced pressure. The residue was purified by chromatography on silica gel, eluting with mixtures of ethyl acetate in hexane, giving the title compound as a light-brown foam (1.04 g, 56%); n$_{max}$ (CH$_2$Cl$_2$) 1801, 1749, 1716 cm$^{-1}$.

b) 4-Methoxybenzyl (5R)-6-[(Z)-(6,7-dihydro-5H-imidazo[2,1-b][1,3]-thiazin-2-yl)methylene]penem-3-carboxylate 4-Methoxybenzyl (5R,6RS,8RS)-6-[acetoxy(6,7-dihydro-5H-imidazo[2,1-b][1,3]thiazin-2-yl)methyl]-6-bromopenem-3-carboxylate (1.04 g, 1.79 mmol) was dissolved in THF (20 ml) and treated sequentially with TMEDA (521 mg, 4.48 mmol), zinc powder (293 mg, 4.48 gm. atom) and glacial acetic acid (296 mg, 4.48 mmol) with vigorous stirring. After 10 minutes, more glacial acetic acid (269 mg, 4.48 mmol) was added and the mixture stirred vigorously for a further 10 minutes. The reaction mixture was partitioned between ethyl acetate and water and filtered through Celite. The phases were separated and the organic phase washed with 1M aqueous potassium hydrogensulphate (3×), saturated brine, saturated aqueous sodium hydrogencarbonate, saturated brine, dried (MgSO$_4$) and evaporated to dryness under reduced pressure. The product was obtained by chromatography on silica gel, eluting with mixtures of ethyl acetate in hexane, as a yellow foam (532 mg, 67%); n$_{max}$ (CH$_2$Cl$_2$) 1773, 1710, 1270 and 1232 cm$^{-1}$; d$_H$ [250 MHz; (CD$_3$)$_2$CO] 2.30–2.42 (2H, m), 3.22–3.33 (2H, m), 3.80 (3H, s), 4.20 (2H, t, J 6Hz), 5.16 (2H, brs), 6.55 (1H, d, J 11Hz), 6.88–6.97 (3H, m), 7.38–7.53 (4H, m).

c) Sodium (5R)-6-[(Z)-(6,7-dihydro-5H-imidazo[2,1-b][1,3]thiazin-2-yl)methylene]penem-3-carboxylate Anisole (2.02 g, 18 mmol) was dissolved in dry dichloromethane (2 ml) under argon and treated with aluminium trichloride (248 mg, 1.8 mmol). When complete solution had been obtained, the mixture was cooled to −40° C. and treated dropwise with a solution of 4-methoxybenzyl (5R)-6-[(Z)-(6,7-dihydro-5H-imidazo[2,1-b][1,3]thiazin-2-yl)methylene]penem-3-carboxylate in dry dichloromethane (10 ml). After 10 minutes at −40° C., the reaction mixture was treated with 0.5M aqueous trisodium citrate (15 ml) and cooling was removed. After 15 minutes at ambient temperature, the mixture was diluted with diethyl ether, water and acetone until two clear phases were obtained. The phases were separated, the aqueous phase washed with diethyl ether and acidified to pH 2 with 5M hydrochloric acid in the presence of ethyl acetate. The phases were separated, the aqueous phase further extracted with ethyl acetate, the extracts combined and washed well with water (4×). The ethyl acetate extract was stirred vigorously in the presence of water and the pH of the aqueous phase adjusted to pH 6.8 with dilute, aqueous sodium hydrogencarbonate. The phases were separated and the aqueous phase freeze-dried. The freeze-dried residue was chromatographed on Diaion HP20SS resin, eluting with mixtures of THF in water, to give the title compound as a bright-yellow, freeze-dried solid (79.5 mg, 37%); l$_{max}$ (H$_2$O) 328 (e dm$^3$ mol$^{-1}$ cm$^{-1}$ 14122) and 247.5 (12142) nm; n$_{max}$ (KBr) 1742, 1672, 1597 cm$^{-1}$; d$_H$ (250 MHz; D$_2$O) 2.18–2.23 (2H, m), 3.17 (2H, t, J 6Hz), 4.04 (2H, t, J 6Hz), 6.44 (1H, s), 6.86 (1H, s), 6.98 (1H, s), 7.35 (1H, s); m/z (F.A.B., +ve ion xenon, glycerol) 366 (MNa$^+$) and 344 (MH$^+$).

EXAMPLE 5

Sodium (5R)-6-[(Z)-(6,7-dihydro-8,8-dioxo-5H-imidazo[2,1-b][1,3]thiazin-2-yl)methylene]penem-3-carboxylate a) 4-Methoxybenzyl (5R,6RS,8RS)-6-[acetoxy (6,7-dihydro-8,8-dioxo-5H-imidazo[2,1-b][1,3]thiazin-2-yl) methyl]-6-bromopenem-3-carboxylate.

Diphenylamine (186 mg, 1.1 mmol) was dissolved in dry, redistillied THF (10 ml) under argon and cooled to −20° C. A solution of n-butyllithium in hexane (2.45M, 410 ml, 1 mmol) was added and cooling removed. After 10 minutes, the mixture was cooled to −70° C. and treated with 4-methoxy-benzyl (5R,6R)-6-bromopenem-3-carboxylate (370 mg, 1 mmol) in dry, redistilled THF (5 ml). The resulting mixture was stirred at −70° C. for 10 minutes then treated at −70° C. with a solution of 6,7-dihydro-5H-imidazo[2,1-b][1,3]thiazine-2-carboxaldehyde-8,8-dioxide (200 mg, 1 mmol) in dry THF (2 ml). This mixture was stirred at −70° C. for 20 minutes before being treated with acetic anhydride (102 mg, 1 mmol) and 4-dimethylamino-pyridine (10 mg). Cooling was removed and the reaction mixture stirred at ambient temperature for 1 h. After 1 h, the volatiles were removed under reduced pressure and the residue partitioned between ethyl acetate and water. The organic phase was washed with water (4×), saturated aq. sodium hydrogencarbonate, water, saturated brine, dried (MgSO$_4$) and evaporated to dryness under reduced pressure. The residue was purified by chromatography on silica gel, eluting with mixtures of ethyl acetate in hexane, to give the title compound (229.6 mg, 37.5%); n$_{max}$ (CH$_2$Cl$_2$) 1802, 1758, 1716, 1330, 1275, 1216 and 168 cm$^{-1}$.

b) 4-methoxybenzyl (5R)-6-[(Z)-(6,7-dihydro-8,8-dioxo-5H-imidazo[2,1-b][1,3]thiazin-2-yl) methylene]penem-3-carboxylate.

4-Methoxy (5R,6RS,8RS)-6-[acetoxy (6,7-dihydro-8,8-dioxo-5H-imidazo [2,1-b][1,3]thiazin-2-yl) methyl]-6-bromopenem-3-carboxylate (410 mg, 0.7 mmol) was dissolved in THF (10 ml) and treated sequentially with TMEDA (195 mg, 1.67 mmol), zinc powder (109 mg, 1.67 g atoms) and glacial acetic acid (101 mg, 1.67 mmol). After 10 minutes more glacial acetic acid (101 mg, 1.67 mmol) was added and the resulting mixture stirred for a further 10 minutes. The reaction mixture was partitioned between ethyl acetate and water and the organic phase washed with 1M aq. sodium hydrogen sulphate (3×), saturated brine, saturated aq. sodium hydrogen carbonate, saturated brine, dried (MgSO$_4$) and evaporated to dryness under reduced pressure. Chromatography on silica gel, eluting with ethyl acetate, gave the title compound as a bright yellow foam (201 mg, 63%); [a]$^D_{25}$+446° (c=0.1% in acetonitrile); lmax (EtOH) 302.5 (e dm3 mol$^{-1}$ cm$^{-1}$ 30,087), 227 (19,073) and 202 (24,890) nm; n$_{max}$ (CH$_2$Cl$_2$) 3134, 1777, 1732, 1711, 1330 and 1235 cm$^{-1}$; d$_H$ [250 MHz; (CD$_3$)$_2$CO)] 2.68–2.77 (2H,m), 3.67–3.72 (2H, m), 3.81 (3H, s), 4.46 (2H, t, J 6Hz), 5.18 (2H, s), 6.59 (1H, d, J 1Hz), 6.94 (2H, d, J 9Hz), 7.11 (1H, d, J 1Hz), 7.41 (2H, d, J 9Hz), 7.50 (1H, s), 7.74 (1H, s); m/z (NH$_3$DCl) 474 (MH$^+$) and 491 (MNH$_4^+$).

c) Sodium (5R)-6-[(Z)-(6,7-dihydro-8,8-dioxo-5H-imidazo [2,1-b][1,3]thiazin-2-yl) methylene]penem-3-carboxylate.

Anisole (1.2 g, 11.4 mmol) was dissolved in dry dichloromethane (1 ml) under argon and the resulting solution treated with aluminium trichloride (152 mg, 1.14 mmol). When a complete solution had been obtained, the solution was cooled to −40° C. and treated at <−30° C. with a solution of 4-methoxybenzyl (5R)-6-[(Z)-(6,7-dihydro-8,8-dioxo-5H-imidazo [2,1-b][1,3]thiazin-2-yl) methylene] penem-3-carboxylate (180 mg 0.38 mmol) in dry dichloromethane (5 ml). After 10 minutes, 0.5M aq. trisodium citrate (10 ml) was added, cooling was removed and the mixture allowed to regain room temperature. The reaction mixture was diluted with diethyl ether, water and acetone until two, clear phses had been obtained. The phases were separated and the aqueous phase wahed with diethyl ether then acidified to pH 2 with 5M hydrochloric acid in the presence of ethyl acetate. The phases were separated and the aqueous phase further extracted with ethyl acetate and the extracts combined, washed with water (5×) then stirred with water. The pH of the aqueous phase was adjusted to 6.8 by addition of dilute, aq. sodium hydrogen carbonate and the phases separated. The aqueous phase was freeze-dried and the resulting orange powder purified by chromatography on HP20SS resin, eluting with water, to give the title compound as a bright orange powder, (54.2 mg, 38%); lmax (H2O) 298 (e dm$^3$ mol$^{-1}$ cm$^{-1}$ 22,425)nm; nmax (KBr) 1750, 1597, 1385, 1317 and 1165 cm$^{-1}$; d$_H$ (250 MHz; D$_2$O) 2.60–2.77 (2H, m), 3.76–3.80 (2H, m), 4.27 (2H, t, J 7Hz), 6.84 (1H, s), 6.96 (1H, s), 7.01 (1H, s), 7.56 (1H, s); m/z (F.A.B., +ve ion xenon, glycerol) 376 (MH$^+$) and 398 (MNa$^+$).

EXAMPLE 6

Sodium (5R)-6-[(Z)-(2,3-dihydroimidazo [2,1-b]thiazol-6-yl) methylene]penem-3-carboxylate (448 mg; 1,36 mmol) was dissolved in the minimum volume of water at ambient temperature and acetone was added until the solution became turbid. The mixture was left to stand for 24 hours at 4° C. and the resulting yellow microcrystalline solid was collected by filtration, washed with acetone and dried under reduced pressure (327 mg; 67% recovery).

EXAMPLE 7

Sodium (5R)-6-[(Z)-(2,3-dihydroimidazo [2,1-b]thiazol-6-yl) methylene penem-3-carboxylate (100 mg; 0.3 mmol) was dissolved in the minimum volume of water at room temperature and diluted with ethanol until the solution became turbid. Trituration gave bright orange crystals, which were collected by filtration, washed with a little ethanol and dried under reduced pressure (42 mg; 42% recovery).

EXAMPLE 8

4-methoxybenzyl (5R)-6-[(Z)-(2,3-dihydroimidazo [2,1-b]thiazol-6-yl)-methylene]penem-3-carboxylate A solution of diphenylamine (2.52 g; 14.85 mmol) dissolved in dry, distilled tetrahydrofuran [THF] (50 mls) was cooled to −20° C. with stirring and treated with a solution of n-butyl lithium (5.7 mls of 2.6M solution in hexanes). The solution was stirred at −20° C. for 10 minutes, then cooled to <−70° C. whereupon a solution of 4-methoxybenzyl 6a-bromopenem-3-carboxylate (5 g; 13.5 mmol) dissolved in dry distilled THF (60 mls) was added dropwise, keeping the reaction temperature <−65° C. Stirring at this temperature was maintained for 15 minutes, whereupon a solution of 2,3-dihydroimidazo[2,1-b]thiazole-6-carboxaldehyde (2.29 g; 14.85 mmol) dissolved in dry dimethylformamide (approx 25 mls) was added over 2–3 mins. Stirring at <−65° C. was maintained for 30 minutes before the addition of acetic anhydride (1.34 mls, 14.2 mmol). The cooling bath was removed and the reaction vessel transfered to an ice bath. Stirring was maintained for 30 minutes whereupon zinc powder (1.34 g; 20.6 mmol), glacial acetic acid (2.32 mls; 40.5 mmol) and N,N,N',N'-tetramethylethylenediamine (3 mls; 20.2 mmol) were added and the reaction allowed to regain ambient temperature over approx. 1 hour. The reaction mixture was then diluted with ethyl acetate (ca 500 mls) and washed with water (4×500 mls) followed by brine (1×250 mls) before drying over magnesium sulphate. Filtration and evaporation gave a residue which was chromatographed on silica gel. Elution with a gradient 50% ¾>75% ethyl acetate/hexane gave the title compound identical in an analytical aspects to that described in example 1b, as a yellow foam (4.01 g, 69.5%).

Sodium (5R)-6-[(Z)-[(2,3-dihydroimidazo[2,1b]thiazol-6-yl)methylene]-penem-3-carboxylate A solution of anisole (59.7 g; 60 mls; 0.55 mol) dissolved in dry dichloromethane [DCM] (60 mls) was cooled to −20° C. with stirring and treated with a solution of ethylaluminium dichloride (39 mls of 1.8M solution in toluene; 70.2 mmol). After stirring for 5 minutes, the reaction was cooled to <−50° C. and treated with a solution of 4-methoxybenzyl (5R)-6-[(Z)-(2,3-dihydroimidayo[2,1-b]-thiazol-6-yl) methylene]penem-3-carboxylate (10 g; 23.4 mmol) dissolved in dry DCM (100 mls) added dropwise, keeping the reaction temperature below −50° C. After stirring for a further 15 minutes, a solution of aqueous trisodium citrate (500 mls of 0.5M soln) was added and the cooling bath removed. Water (500 mls) was added and the pH of the reaction mixture adjusted to 7.2 with aqueous sodium hydrogen carbonate. Diethyl ether (500 mls) was added and the phases separated. The organic phase was further extracted with water, (2×100 mls), the combined aqueous solution was washed with diethyl ether (2×250 mls) before evaporating briefly to remove residual organic solvent. The pH of the aqueous soln. was further adjusted to 7.5 before chromatography on Dianion HP20SS eluting with water. The fractions were combined and reduced in volume by reverse osmosis to give, after freeze drying, the title compound as a yellow solid, having identical analytical properties to those of the compound described in example 1c (4.98 g, 65%). The compound was crystallized under similar conditions to that in example 6.

EXAMPLE 9

The in-vitro synergistic activity of the compound of Example 1 above (i.e sodium (5R)-6-[(Z)-(2,3-dihydroimidazo[2,1-b]thiazol-6-yl)methylene]penem-3-carboxylate) with ceftazidime was investigated.

The presence of 1 $\mu$g/ml of the compound of Example 1 was found to reduce the MIC of ceftazidime against *B. fragilis* from around 7 $\mu$g/ml to around 4 $\mu$g/ml. Similarly the presence of 1 $\mu$g/ml of the compound of Example 1 was found to reduce the MIC of ceftazidime against a strain of Enterobacter producing extended spectrum β-lacatmase enzymes from around 7 $\mu$g/ml to around 2 $\mu$g/ml. In a population of *E. cloacae* growing in the presence of ceftazidime at a concentration of 0.5 MIC a population of cells showing high-level resistance to ceftazidime was rapidly selected in vitro. The presence of the compound of Example 1 reduced the rate of emergence of resistant isolates dramatically. In addition the final level of resistance seen with the combination of ceftazidime and the compound of Example 1 was much lower than that observed with ceftazidime alone.

EXAMPLE 10

The in-vitro synergistic activity of the compound of Example 1 above (i.e sodium (5R)-6-[(Z)-(2,3-dihydroimidazo[2,1-b]thiazol-6-yl)methylene]penem-3-carboxylate) with cefotaxime was investigated.

Effective synergy with cefotaxime was observed with 1 $\mu$g/ml of this compound against *B. fragilis*, and strains of Enterobacteriaceae producing extended spectrum β-lactamases.

The MIC (minimum inhibitory concentration) of cefotaxime against one TEM-3 producing strain of *K. pneumoniae* was measured. In the absence of the compound of Example 1 the MIC of cefotaxime was 64 $\mu$g/ml. Concentrations of the compound of Example 1 as low as 0.25 $\mu$g/ml reduced the MIC of cefotaxime to below 1 $\mu$g/ml. When a similar titration was carried out against a strain of *Ent. cloacae* producing high levels of Class 1-β-lactamases constitutively, a cefotaxime MIC <1 $\mu$g/ml was achieved in the presence of 1 $\mu$g/ml of the compound of Example 1.

EXAMPLE 11

Preliminary experimental infection studies have demonstrated the in vivo efficacy of the compound of Example 1, when coadministered parenterally with cefotaxime, against infections caused by different bacterial pathogens that produce β-lactamase, the compound protecting cefotaxime (Table 1) from inactivation by a variety of important β-lactamases in an experimental model of intraperitoneal infection.

In these studies, mice were infected intraperitoneally with a lethal challenge inoculum of strains of either *Klebsiella pneumoniae* (520), producing extended-spectrum TEM type β-lactamase, (TEM-3) or *Enterobacter cloacae* (4593) producing high levels of derepressed class (AmpC) β-lactamase. Virulence of all strains was enhanced by suspending the bacteria in hog gastric mucin prior to infection.

Mice were dosed subcutaneously at 1 and 5 hours post-infection, with either cefotaxime alone or coadministered with the β-lactamase inhibitor at 1 mg/kg or 5 mg/kg.

TABLE 1

| Efficacy of Cefotaxime Alone and with Example 1 in Mouse Intraperitoneal Infections | | | |
|---|---|---|---|
| | Cefotaxime CD50[1] (mg/kg) | | |
| Organism | Alone | + 1 mg/kg Example 1 | + 5 mg/kg Example 1 |
| *K. pneumoniae* Test 1 | 42 | 36 | 13.6 |
| Test 2 | 54 | 26 | 8 |
| *E. cloacae* 4593 Test 1a | 240 | 170 | 48 |
| Test 2a | 400 | 170 | 32 |

[1]$CD_{50}$ (dose protecting 50% of animals from lethal infection) calculated from groups of 5 animals per test, subjected to a range of 4 dose levels (4-fold serial dilutions)

Efficacy was assessed by the number of animal surviving at 4 days after infection, and the total dose that protected 50% of treated animals ($CD_{50}$ value) was calculated. The results of these studies showed consistent protection of animals intraperitoneally infected with cefotaxime-resistant strains of *K. pneumoniae* (520) and *E. cloacae* (4593), which received cefotaxime and the compound of Example 1 compared with those receiving cefotaxime alone.

EXAMPLE 12

Table 2 shows the in-vitro synergistic activity of the compound of Example 1 above (i.e sodium (5R)-6-[(Z)-(2, 3-dihydroimidazo[2,1-b]thiazol-6-yl)methylene]penem-3- carboxylate) with amoxycillin, expressed in terms of minimum inhibitory concentration (MIC).

TABLE 2

| | | | Amoxycillin | |
| --- | --- | --- | --- | --- |
| | | | + Example 1 at | |
| Organism | β-lactamase | Alone | 0.25 µg/ml | 1 µg/ml |
| Ent. cloacae N1 | 1 (inducible expression) | >256 | 16 | 4 |
| Ent. cloacae P99 | 1 (high constitutive expression) | >256 | 256 | 32 |
| S. aureus Russell | 2a | 128 | 1 | — |
| E. coli JT39 | 2b (low expression) | >256 | 4 | 4 |
| P. coli JT4 | 2b (high expression) | >256 | 8 | 2 |
| P. mirabilis C889 | 2c | >256 | 64 | 16 |
| E. coli P91 | 2d | >256 | — | 8 |
| P. vulgaris C | 2e | 32 | 0.5 | 0.5 |

EXAMPLE 13

Preliminary experimental infection studies have demonstrated the in vivo efficacy of the compound of Example 1, when coadministered parenterally with amoxycillin against infections caused by different bacterial pathogens that produce β-lactamase, the compound protecting amoxycillin (Table 3) from inactivation by a variety of important β-lactamases in an experimental model of intraperitoneal infection.

In these studies, mice were infected intraperitoneally with a lethal challenge inoculum of strains of *Escherichia coli* (E96), producing TEM-1 β-lactamase, for tests to protect amoxycillin. Virulence of all strains was enhanced by suspending the bacteria in hog gastric mucin prior to infection.

Mice were dosed subcutaneously at 1 and 5 hours post-infection, with either amoxycillin alone or coadministered with the β-lactamase inhibitor at 2 mg/kg.

TABLE 3

Efficacy of amoxycillin alone and co-administered with Example 1 against an Intraperitoneal Infection of *E. coli* E96 (TEM-1) in mice.

| | CD50[1] (mg/kg) of Amoxycillin | |
| --- | --- | --- |
| | Alone | + 2 mg/kg Example 1 |
| Test 1 | >1000 | 1.0 |
| Test 2 | 300 | <1.5 |

Efficacy was assessed by the number of animal surviving at 4 days after infection, and the total dose that protected 50% of treated animals ($CD_{50}$ value) was calculated. The results of two studies showed amoxycillin to be markedly more effective in protecting those animals that received coadministration with the compound of Example 1, than those that received amoxycillin alone (Table 3).

We claim:

1. A pharmaceutical formulation comprising a penem of formula (I):

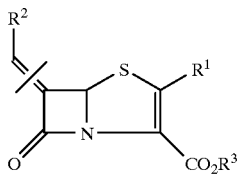

in which:

$R^1$ is hydrogen or, $-R^6$ or $-SR^6$ where $R^6$ is an unsubstituted or substituted ($C_1$–$C_{10}$)hydrocarbon or heterocyclyl group;

$R^2$ is a fused bicyclic heterocyclic ring system of the formula:

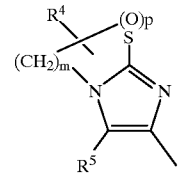

wherein $R^4$ and $R^5$ are independently selected from the group consisting of hydrogen, ($C_{1-6}$)alkanoyl, ($C_{1-6}$) alkanoyloxy, heterocyclyl, amino, ($C_{1-6}$) alkanoylamino, (mono or di)-($C_{1-6}$)alkylamino, hydroxy, ($C_{1-6}$)alkoxy, sulpho, mercapto, ($C_{1-6}$) alkylthio, ($C_{1-6}$)alkylsulphinyl, ($C_{1-6}$)alkyl-sulphonyl, heterocyclylthio, arylthio, sulphamoyl, carbamoyl, amidino, guanidino, nitro, halogen, carboxy, carboxy salts, carboxy esters, arylcarbonyl, and heterocyclyl-carbonyl groups, and also unsubstituted or substituted ($C_{1-6}$)alkyl, ($C_{2-6}$)alkenyl, ($C_{2-6}$)alkynyl, aryl, or an aryl($C_{1-6}$)alkyl group, m is 2 or 3; p is zero, 1 or 2; and $R^3$ is hydrogen, a salt-forming cation or an ester-forming group; and the symbol ═/═ indicates that the double bond may be in either the E or Z configuration; and a pharmaceutically acceptable carrier; a β-lactam antibiotic selected from the group consisting of ceftazidime, cefotaxime, amoxycillin, and piperacillin, and pharmaceutically acceptable derivatives thereof.

2. A formulation according to claim 1 wherein the compound of formula (I) is sodium (5R)-6-[(Z)-(2,3-dihydroimidazo[2,1-b]thiazol-6-yl) methylene]penem-3-carboxylate.

3. A formulation according to claim 1 formulated for parenteral administration.

4. A method of treating or preventing bacterial infections, which method comprises administering to a human or animal an antibacterially effective amount of a formulation according to claim 1.

5. A process for the preparation of a formulation in accordance with claim 1, which comprises mixing a therapeutically effective amount of a compound of formula (I) as defined in claim 1 with a therapeutically effective amount of a β-lactam antibiotic selected from the group consisting of ceftazidime, cefotaxime, amoxycillin and piperacillin, and pharmaceutically acceptable derivatives thereof, and a pharmaceutically acceptable carrier.

6. A method of inhibiting hydrolysis by β-lactamase of a β-lactam antibiotic selected from the group consisting of ceftazidime, cefotaxime, amoxycillin and piperacillin, and pharmaceutically acceptable derivatives thereof, which method comprises administering to a human or animal a β-lactamase inhibitory amount of a compound of formula (I) as defined in claim 1.

7. A pharmaceutical formulation comprising a penem of formula (I):

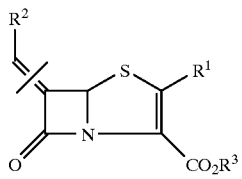

in which:
R$^1$ is hydrogen, —R$^6$ or —SR$^6$ where R$^6$ is an unsubstituted or substituted (C$_1$–C$_{10}$)hydrocarbon or heterocyclyl group;
R$^2$ is a fused bicyclic heterocyclic ring system of the formula:

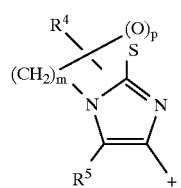

wherein R$^4$ and R$^5$ are independently selected from the group consisting of hydrogen (C$_{1-6}$)alkanoyl, (C$_{1-6}$) alkanoyloxy, heterocyclyl, amino, (C$_{1-6}$) alkanoylamino, (mono or di)-(C$_{1-6}$)alkylamino, hydroxy, (C$_{1-6}$)alkoxy, sulpho, mercapto, (C$_{1-6}$) alkylthio, (C$_{1-6}$)alkylsulphinyl, (C$_{1-6}$)alkylsulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted (C$_{1-6}$)alkyl, (C$_{2-6}$)alkenyl, (C$_{2-6}$)alkynyl, aryl, and aryl (C$_{1-6}$)alkyl groups; m is 2 or 3; p is zero, 1 or 2; and R$^3$ is hydrogen, a salt-forming cation or an ester-forming group; and the symbol =/= indicates that the double bond may be in either the E or Z configuration; the β-lactam antibiotic cefotaxime; or a pharmaceutically acceptable derivative of either thereof; and a pharmaceutically acceptable carrier.

8. A formulation according to claim 7 wherein the compound of formula (I) is sodium (5R)-6-[(Z)-(2,3-dihydroimidazo[2,1-b]thiazol-6-yl)methylene]penem-3-carboxylate.

9. A formulation according to claim 7 formulated for parenteral administration.

10. A method of treating or preventing bacterial infections, which method comprises administering to a human or animal an antibacterially effective amount of a formulation according to claim 7.

11. A process for the preparation of a formulation in accordance with claim 7, which comprises mixing a therapeutically effective amount of a compound of formula (I) or a pharmaceutically acceptable derivative thereof as defined in claim 7 with a therapeutically effective amount of the β-lactam antibiotic cefotaxime or a pharmaceutically acceptable derivative thereof, and a pharmaceutically acceptable carrier.

12. A method of inhibiting hydrolysis by β-lactamase of the β-lactam antibiotic cefotaxime or a pharmaceutically acceptable derivative thereof which method comprises administering to a human or animal a β-lactamase inhibitory amount of a compound of formula (I) or a pharmaceutically acceptable derivative thereof as defined in claim 7.

13. A pharmaceutical formulation comprising a penem of formula (I):

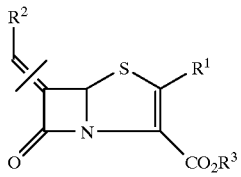

in which:
R$^1$ is hydrogen, —R$^6$ or —SR$^6$ where R$^6$ is an unsubstituted or substituted (C$_1$–C$_{10}$)hydrocarbon or heterocyclyl group;
R$^2$ is a fused bicyclic heterocyclic ring system of the formula:

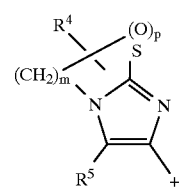

wherein R$^4$ and R$^5$ are independently selected from the group consisting of hydrogen (C$_{1-6}$)alkanoyl, (C$_{1-6}$) alkanoyloxy, heterocyclyl, amino, (C$_{1-6}$) alkanoylamino, (mono or di)-(C$_{1-6}$)alkylamino, hydroxy, (C$_{1-6}$)alkoxy, sulpho, mercapto, (C$_{1-6}$) alkylthio, (C$_{1-6}$)alkylsulphinyl, (C$_{1-6}$)alkylsulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted (C$_{1-6}$)alkyl, (C$_{2-6}$)alkenyl, (C$_{2-6}$)alkynyl, aryl, and aryl (C$_{1-6}$)alkyl groups; m is 2 or 3; p is zero, 1 or 2; and R$^3$ is hydrogen, a salt-forming cation or an ester-forming group; and the symbol =/= indicates that the double bond may be in either the E or Z configuration; the β-lactam antibiotic amoxycillin; or a pharmaceutically acceptable derivative of either thereof; and a pharmaceutically acceptable carrier.

14. A formulation according to claim 13 wherein the compound of formula (I) is sodium (5R)-6-[(Z)-(2,3-dihydroimidazo[2,1-b]thiazol-6-yl)methylene]penem-3-carboxylate.

15. A formulation according to claim 13 formulated for parenteral administration.

16. A method of treating or preventing bacterial infections, which method comprises administering to a human or animal an antibacterially effective amount of a formulation according to claim 13.

17. A process for the preparation of a formulation in accordance with claim 13, which comprises mixing a therapeutically effective amount of a compound of formula (I) or a pharmaceutically acceptable derivative thereof as defined in claim 13 with a therapeutically effective amount of the β-lactam antibiotic amoxycillin or a pharmaceutically acceptable derivative thereof, and a pharmaceutically acceptable carrier.

18. A method of inhibiting hydrolysis by β-lactamase of the β-lactam antibiotic amoxycillin or a pharmaceutically acceptable derivative thereof which method comprises administering to a human or animal a β-lactamase inhibitory amount of a compound of formula (I) or a pharmaceutically acceptable derivative thereof as defined in claim 13.

19. A pharmaceutical formulation comprising a penem of formula (I):

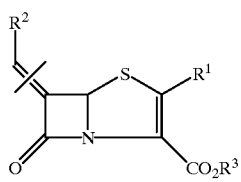
(I)

in which:

R$^1$ is hydrogen, —R$^6$ or —SR$^6$ where R$^6$ is an unsubstituted or substituted (C$_1$–C$_{10}$)hydrocarbon or heterocyclyl group;

R$^2$ is a fused bicyclic heterocyclic ring system of the formula:

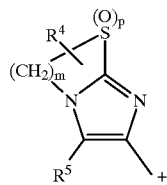

wherein R$^4$ and R$^5$ are independently selected from the group consisting of hydrogen, (C$_{1-6}$)alkanoyl, (C$_{1-6}$)alkanoyloxy, heterocyclyl, amino, (C$_{1-6}$)alkanoylamino, (mono or di)-(C$_{1-6}$)alkylamino, hydroxy, (C$_{1-6}$)alkoxy, sulpho, mercapto, (C$_{1-6}$)alkylthio, (C$_{1-6}$)alkylsulphinyl, (C$_{1-6}$)alkylsulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted (C$_{1-6}$)alkyl, (C$_{2-6}$)alkenyl, (C$_{2-6}$)alkynyl, aryl, and aryl (C$_{1-6}$)alkyl groups; m is 2 or 3; p is zero, 1 or 2; and R$^3$ is hydrogen, a salt-forming cation or an ester-forming group; and the symbol $=\!\!/\!\!=$ indicates that the double bond may be in either the E or Z configuration; the β-lactam antibiotic piperacillin; or a pharmaceutically acceptable derivative of either thereof: and a pharmaceutically acceptable carrier.

20. A formulation according to claim 19 wherein the compound of formula (I) is sodium (5R)-6-[(Z)-(2,3-dihydroimidazo[2,1-b]thiazol-6-yl)methylene]penem-3-carboxylate.

21. A formulation according to claim 19 formulated for parenteral administration.

22. A method of treating or preventing bacterial infections, which method comprises administering to a human or animal an antibacterially effective amount of a formulation according to claim 19.

23. A process for the preparation of a formulation in accordance with claim 19, which comprises mixing a therapeutically effective amount of a compound of formula (I) or a pharmaceutically acceptable derivative thereof as defined in claim 11 with a therapeutically effective amount of the β-lactam antibiotic piperacillin or a pharmaceutically acceptable derivative thereof, and a pharmaceutically acceptable carrier.

24. A method of inhibiting hydrolysis by β-lactamase of the β-lactam antibiotic piperacillin or a pharmaceutically acceptable derivative thereof which method comprises administering to a human or animal a β-lactamase inhibitory amount of a compound of formula (I) or a pharmaceutically acceptable derivative thereof as defined in claim 19.

* * * * *